United States Patent
Larimer et al.

(10) Patent No.: US 10,577,511 B2
(45) Date of Patent: Mar. 3, 2020

(54) STRETCHABLE HYDROPHOBIC MATERIALS AND METHODS FOR MAKING THE SAME

(71) Applicant: Battelle Memorial Institute, Richland, WA (US)

(72) Inventors: Curtis J. Larimer, Richland, WA (US); Raymond S. Addleman, Benton City, WA (US); Michelle R. Brann, Richland, WA (US); George T. Bonheyo, Sequim, WA (US); Eric M. Winder, Sequim, WA (US)

(73) Assignee: Battelle Memorial Institute, Richland, WA (US)

( * ) Notice: Subject to any disclaimer, the term of this patent is extended or adjusted under 35 U.S.C. 154(b) by 431 days.

(21) Appl. No.: 15/410,225

(22) Filed: Jan. 19, 2017

(65) Prior Publication Data

US 2017/0204279 A1    Jul. 20, 2017

Related U.S. Application Data

(60) Provisional application No. 62/281,048, filed on Jan. 20, 2016.

(51) Int. Cl.
*C09D 7/62* (2018.01)
*C09D 5/00* (2006.01)
(Continued)

(52) U.S. Cl.
CPC ............ *C09D 7/62* (2018.01); *A61B 42/00* (2016.02); *A61B 42/10* (2016.02); *B05D 1/12* (2013.01); *B05D 5/00* (2013.01); *B05D 7/548* (2013.01); *C09D 5/00* (2013.01); *C09D 7/61* (2018.01); *C09D 7/65* (2018.01); *C09D 107/02* (2013.01); *C09D 109/04* (2013.01);
(Continued)

(58) Field of Classification Search
None
See application file for complete search history.

(56) References Cited

U.S. PATENT DOCUMENTS 3,931,428 A    1/1976 Reick
4,913,760 A    4/1990 Benson et al.
(Continued)

FOREIGN PATENT DOCUMENTS

WO    WO 01/19932    3/2001
WO    WO2012/003004    1/2012
(Continued)

OTHER PUBLICATIONS

Daniel, D., et al., "Lubricant-infused micro/nano-structured surfaces with tunable dynamic omniphobicity at high temperatures," *Applied Physics Letters*, 102(23):231603-1-231603-4 (Jun. 2013).
(Continued)

*Primary Examiner* — Shamim Ahmed
*Assistant Examiner* — Bradford M Gates
(74) *Attorney, Agent, or Firm* — Klarquist Sparkman, LLP

(57) ABSTRACT

Hydrophobic materials, processes for their production, and uses thereof are described. The materials can be made with silica or polytetrafluoroethylene particles embedded into a liquid polymer. The hydrophobic materials are stretchable.

20 Claims, 25 Drawing Sheets

(51) Int. Cl.
| | |
|---|---|
| *C09D 109/04* | (2006.01) |
| *A61B 42/10* | (2016.01) |
| *C09D 7/65* | (2018.01) |
| *A61B 42/00* | (2016.01) |
| *C09D 7/61* | (2018.01) |
| *C09D 107/02* | (2006.01) |
| *B05D 1/12* | (2006.01) |
| *B05D 5/00* | (2006.01) |
| *B05D 7/00* | (2006.01) |
| *C08K 3/36* | (2006.01) |
| *A61B 17/00* | (2006.01) |
| *B05D 5/08* | (2006.01) |
| *B05D 7/02* | (2006.01) |

(52) U.S. Cl.
CPC ...... *A61B 2017/00526* (2013.01); *B05D 5/08* (2013.01); *B05D 7/02* (2013.01); *B05D 2451/00* (2013.01); *C08K 3/36* (2013.01)

(56) References Cited

U.S. PATENT DOCUMENTS

| | | | |
|---|---|---|---|
| 4,933,237 | A | 6/1990 | Krenceski et al. |
| 5,976,297 | A * | 11/1999 | Oka ........................ B29C 70/60 156/241 |
| 6,117,555 | A | 9/2000 | Fujimori et al. |
| 6,326,111 | B1 | 12/2001 | Chambers et al. |
| 6,495,624 | B1 | 12/2002 | Brown |
| 6,800,354 | B2 | 10/2004 | Baumann et al. |
| 7,772,456 | B2 | 8/2010 | Zhang et al. |
| 8,535,779 | B1 | 9/2013 | Smith et al. |
| 8,574,704 | B2 | 11/2013 | Smith et al. |
| 8,580,027 | B1 | 11/2013 | Campos et al. |
| 8,614,003 | B2 | 12/2013 | Ma et al. |
| 8,741,432 | B1 | 6/2014 | Campos et al. |
| 8,940,361 | B2 | 1/2015 | Smith et al. |
| 9,121,306 | B2 | 9/2015 | Aizenberg et al. |
| 9,121,307 | B2 | 9/2015 | Aizenberg et al. |
| 9,254,496 | B2 | 2/2016 | Dhiman et al. |
| 2005/0112326 | A1 | 5/2005 | Nun et al. |
| 2005/0118433 | A1 | 6/2005 | Oles et al. |
| 2007/0141305 | A1 | 6/2007 | Kasal |
| 2008/0229929 | A1* | 9/2008 | Marcoon ............... A62B 23/025 96/296 |
| 2009/0042469 | A1 | 2/2009 | Simpson |
| 2009/0104347 | A1 | 4/2009 | Van Benthem |
| 2009/0136741 | A1 | 5/2009 | Zhang et al. |
| 2010/0004373 | A1 | 1/2010 | Zhu et al. |
| 2010/0035039 | A1 | 2/2010 | Jing et al. |
| 2011/0021698 | A1 | 1/2011 | Vyörykkä et al. |
| 2011/0033663 | A1 | 2/2011 | Svec et al. |
| 2011/0045247 | A1 | 2/2011 | Nun et al. |
| 2012/0052241 | A1 | 3/2012 | King et al. |
| 2012/0058330 | A1 | 3/2012 | Smith et al. |
| 2014/0106127 | A1 | 4/2014 | Lyons et al. |
| 2014/0147627 | A1 | 5/2014 | Aizenberg et al. |
| 2014/0155522 | A1* | 6/2014 | Simpson ............... C09D 127/22 523/400 |
| 2014/0165263 | A1 | 6/2014 | Pham et al. |
| 2014/0290731 | A1 | 10/2014 | Aizenberg et al. |
| 2014/0290732 | A1 | 10/2014 | Aizenberg et al. |
| 2014/0328999 | A1 | 11/2014 | Aizenberg et al. |
| 2015/0005424 | A1 | 1/2015 | Jones et al. |
| 2015/0152270 | A1 | 6/2015 | Aizenberg et al. |
| 2015/0175814 | A1 | 6/2015 | Aizenberg et al. |
| 2015/0210951 | A1 | 7/2015 | Aizenberg et al. |
| 2016/0032074 | A1 | 2/2016 | Aizenberg et al. |
| 2017/0058130 | A1 | 3/2017 | Addleman et al. |
| 2018/0305543 | A1* | 10/2018 | Agrawal ................. C08L 23/12 |

FOREIGN PATENT DOCUMENTS

| | | |
|---|---|---|
| WO | WO2012/100100 | 7/2012 |
| WO | WO2013/115868 | 8/2013 |
| WO | WO2014/012039 | 1/2014 |
| WO | WO2014/012080 | 1/2014 |
| WO | WO2014/019809 | 2/2014 |
| WO | WO2014/035742 | 5/2014 |
| WO | WO 2014/094042 | 6/2014 |
| WO | WO2015/012910 | 1/2015 |

OTHER PUBLICATIONS

Dickson, M.N., "BioFocus: Slippery Liquid-Infused Porous Surface Coating on Steel Resists Biofouling," *MRS Bulletin*, 41(1):9 (Jan. 2016).

Epstein, A.K., et al., "Liquid-infused Structured Surfaces with Exceptional Anti-biofouling Performance," *Proceedings of the National Academy of Sciences*, 109(33):13182-13187 (Aug. 2012).

Girotti et al., "Improved detection of toxic chemicals using bioluminescent bacteria," *Analytica Chimica Acta*, 471(1):113-120 (Oct. 2002).

Grinthal, A., et al., "Mobile Interfaces: Liquids as a Perfect Structural Material for Multifunctional, Antifouling Surfaces," *Chemistry of Materials*, 26(1):698-708 (Oct. 2013).

Howell, C., et al., "Self-Replenishing Vascularized Fouling-Release Surfaces," *ACS Applied Materials & Interfaces*, 6(15):13299-13307 (Jul. 2014).

Howell, C., et al., "Stability of Surface-Immobilized Lubricant Interfaces Under Flow," *Chemistry of Materials*, 27(5):1792-1800 (Feb. 2015).

International Search Report and Written Opinion for PCT/US2016/049019 (dated Dec. 16, 2016).

MacCallum, N., et al., "Liquid-Infused Silicone as a Biofouling-Free Medical Material," *ACS Biomaterials Science & Engineering*, 1(1):43-51 (Dec. 2014).

Office Action from United States Patent Office for U.S. Appl. No. 14/839,471, (dated Oct. 4, 2017).

Park et al., "Potential Impact of Seawater Uranium Extraction on Marine Life," *Industrial & Engineering Chemistry Research*, 55(15):4278-4284 (Feb. 2016).

Parvez et al., "A review on advantages of implementing luminescence inhibition test (*Vibrio fischeri*) for acute toxicity prediction of chemicals," *Environment International*, 32(2):265-268 (Feb. 2006).

Tesler, A.B., et al., "Extremely Durable Biofouling-Resistant Metallic Surfaces Based on Electrodeposited Nanoporous Tungstite Films on Steel," *Nature Communications*, 6(Article 8649):10 pgs. (Oct. 2015).

Tian, et al., "Moving superhydrophobic surfaces toward real-world applications," *Science*, 352(6282):142-143 (Apr. 2016).

Wang, N., et al., "Fabrication of superhydrophobic and lyophobic slippery surfaces on steel substrate," *Applied Surface Science*, 387:1219-1224 (Nov. 2016).

Wang, P., et al., "Slippery Liquid-Infused Porous Surfaces Fabricated on Aluminum as a Barrier to Corrosion Induced by Sulfate Reducing Bacteria," *Corrosion Science*, 93:159-166 (Apr. 2015).

Zhang, P., et al., "Anti-adhesion effects of liquid infused textured surfaces on high temperature stainless steel for soft tissue," *Applied Surface Science*, 385:249-256 (Nov. 2016).

Anand, S., et al., "Enhanced Condensation on Lubricant-Impregnated Nanotextured Surfaces," *ACS Nano*, 6(11):10122-10129 (Oct. 2012).

Bhadury, P., et al., "Exploitation of Marine Algae: Biogenic Compounds for Potential Antifouling Applications," *Planta*, 219(4):561-578 (Aug. 2004).

Chen, L., et al., "Transparent Slippery Surfaces Made with Sustainable Porous Cellulose Lauroyl Ester Films," *Applied Materials & Interfaces*, 6:6969-6976 (Apr. 2014).

Dyett, B., et al., "Toward Superhydrophobic and Durable Coatings: Effect of Needle vs. Crater Surface Architecture," *ACS Appl. Mater. Interfaces*, 6:9503-9507 (May 2014).

Godwin, L. S., "Hull Fouling of Maritime Vessels as a Pathway for Marine Species Invasions to the Hawaiian Islands," *Proceedings of a Workshop on Current Issues and Potential Management Strategies*, Honolulu, HI (Feb. 12-13, 2003).

(56) References Cited

OTHER PUBLICATIONS

Hoshian, S., et al., "Robust Superhydrophobic Silicon without a Low Surface-Energy Hydrophobic Coating," *ACS Appl. Mater. Interfaces*, 7:941-949 (Dec. 2014).

Hou, X., et al., "Preparation of polypropylene superhydrophobic surface and its blood compatibility," *Colloids and Surfaces B: Biointerfaces*, 80:247-250 (Jun. 2010).

Huang, X., et al., "Omniphobic Slippery Coatings Based on Lubricant-Infused Porous Polyelectrolyte Multilayers," *ACS Macro Letters*, 2(9):826-829 (Sep. 2013).

International Search Report and Written Opinion for PCT/US2017/014061, 8 pages (dated Apr. 7, 2017).

Karapanagiotis, I., et al., "From Hydrophobic to Superhydrophobic and Superhydrophilic Siloxanes by Thermal Treatment," *Langmuir*, 30:13235-13243 (Oct. 2014).

Kim, P., et al., "Hierarchical or Not? Effect of the Length Scale and Hierarchy of the Surface Roughness on Omniphobicity of Lubricant-Infused Substrates," *Nano Letters*, 13(4):1793-1799 (Mar. 2013).

Kim, P., et al., "Liquid-Infused Nanostructured Surfaces with Extreme Anti-Ice and Anti-Frost Performance," *ACS Nano*, 6(8):6569-6577 (Jun. 2012).

Kondrashov, V., et al., "Microcones and Nanograss: Toward Mechanically Robust Superhydrophobic Surfaces," *Langmuir*, 30:4342-4350 (Mar. 2014).

Luong-Van, E., et al., "Review: Micro- and nanostructured surface engineering for biomedical applications," *J. Mater. Res.*, 28(2):165-174 (Jan. 2013).

Mao, C., et al., "Preparation of lotus-leaf-like polystyrene micro- and nanostructure films and its blood compatibility," *J. Mater. Chem.*, 19:9025-9029 (Oct. 2009).

Okada, I., et al., "High-Transparency, Self-Standable Gel-SLIPS Fabricated by a Facile Nanoscale Phase Separation," *ACS Applied Materials & Interfaces*, 6(3):1502-1508 (2014).

Rykaczewski, K., et al., "Mechanism of Frost Formation on Lubricant-Impregnated Surfaces," *Langmuir*, 29(17):5230-5238 (Apr. 2013).

Scardino, A. J., et al., "Mini Review: Biomimetic Models and Bioinspired Surfaces for Fouling Control," *Biofueling*, 27(1):73-86 (Jan. 2011).

Schachter, B., "Slimy Business—The Biotechnology of Biofilms," *Nature Biotechnology*, 21(4):361-365 (May 2003).

Schultz, M. P., et al., "Economic Impact of Biofouling on a Naval Surface Ship," *Biofueling*, 27(1):87-98 (Jan. 2011).

Smith, J. D., et al., "Droplet Mobility on Lubricant-Impregnated Surfaces," *Soft Matters*, 9(6):1772-1780 (2013).

Sun, D., et al., "No Platelet Can Adhere—Largely Improved Blood Compatibility on Nanstructured Superhydrophobic Surfaces," *Small*, 1(10):959-963 (Aug. 2005).

Venkatesan, R., et al., "Macrofouling Control in Power Plants," Biofouling and Biofilm Processes Section, Water and Steam Chemistry Division, BARC Facilities, Indira Gandhi Center for Atomic Research Campus, Kalpakkam , 603 102, India, 265-291 (2008).

Vongsetskul, T., et al., "Antimicrobial nitrile gloves coated by electrospun trimethylated chitosan-loaded polyvinyl alcohol ultrafine fibers," *Polym. Bull.*, 72:2285-2296 (Jun. 2015).

Wong, T. -S., et al., "Bioinspired Self-Repairing Slippery Surfaces With Pressure-Stable Omniphobicity," *Nature*, 477:443-447 (Sep. 2011).

Xiu, Y., et al., "Mechanically robust superhydrophobicity on hierarchically structured Si surfaces," *Nanotechnology*, 21:155705-155709 (Mar. 2010).

Zhao, Y., et al., "Fabrication of Super-Hydrophobic Surfaces with Long-Term Stability," *Journal of Dispersion Science and Technology*, 32(7):969-974 (Jun. 2011).

Zhu, X., et al., "Robust superhydrophobic surfaces with mechanical durability and easy repairability," *J. Mater. Chem.*, 21:15793-15797 (Sep. 2011).

Zhu, X., et al., "Facile fabrication of a superhydrophobic fabric with mechanical stability and easy-repairability," *Journal of Colloid and Interface Science*, 380:182-186 (May 2012).

* cited by examiner

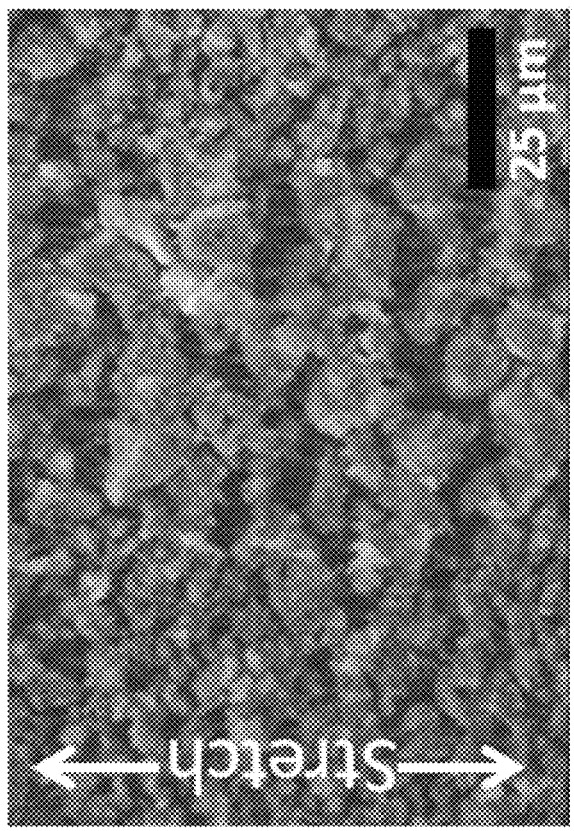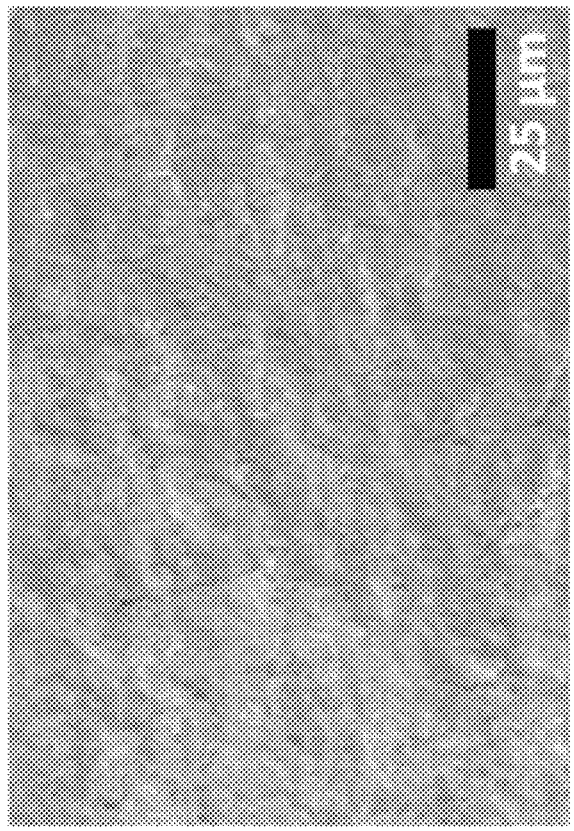
FIG. 12

STRETCHABLE HYDROPHOBIC MATERIALS AND METHODS FOR MAKING THE SAME

CROSS REFERENCE TO RELATED APPLICATION

This application claims the benefit of U.S. Provisional Patent Application No. 62/281,048, filed Jan. 20, 2016, which is hereby incorporated by reference.

ACKNOWLEDGMENT OF GOVERNMENT SUPPORT

This invention was made with government support under Contract DE-AC05-76RL01830 awarded by the U.S. Department of Energy. The government has certain rights in the invention.

BACKGROUND

Synthetic hydrophobic materials that readily shed water and other liquids are useful in a variety of applications. For example, personal protective equipment (PPE) is a persistent source of hospital acquired infections due to cross-contamination. The emergence of Ebola virus in West Africa was a global public health threat, as the virus is transmitted by contact with bodily fluids from patients experiencing bleeding, vomiting and/or diarrhea. Healthcare workers who treat gravely ill patients are among those with the highest exposure risk to the virus, because PPE that retains infectious materials can transfer it to other surfaces, including the user. Similar liquid transfers may also contribute to additional hospital-acquired infections. Comparable exposure risks exist in laboratory, industrial, and field settings. There is a need for synthetic hydrophobic materials that may be used for PPE that does not retain liquids, to limit transfer of infectious materials.

SUMMARY

PPE with modified wetting behavior, such that liquids are shed easily, aid in the reduction of the risks of transmitting infectious disease such as Ebola. During normal use, PPE is subject to movement, including stretching and abrasion, and may incorporate non-toxic materials. Embodiments of the presently disclosed PPE would also reduce risks to first responders in case of a chemical or biological incident. There is a need for highly water-repellent PPE that stretch without suffering loss of water repellency and which are durable to abrasion. Additionally, water repellent flexible materials have applications beyond PPE. Presented herein are durable and stretchable hydrophobic materials and processes for making the same, which stretchable hydrophobic materials can be incorporated into a variety of articles including PPE.

Embodiments of processes to form the stretchable hydrophobic materials are presented. An embodiment of these processes may include applying a stretchable, hydrophobic coating to a substrate by dispensing liquid polymer to the substrate forming a layer of liquid polymer thereon, and embedding a plurality of hydrophobic particles in the layer of liquid polymer, to form a coating on the substrate that is hydrophobic and stretchable. The process may also include the step of drying the liquid polymer.

In an embodiment, the substrate comprises latex, nitrile, or mixtures thereof. In certain embodiments, the liquid polymer comprises latex, nitrile, or polydimethylsiloxane. In some embodiments, the hydrophobic particles comprise silica or polytetrafluoroethylene. In further embodiments, the hydrophobic particles comprise a hydrophobic shell, for example, silica particles comprising a shell comprising hexamethyldisilazane or polydimethylsiloxane.

Certain embodiments of the stretchable, hydrophobic materials made with the processes presented herein exhibit a significant increase in water contact angle when the stretchable, hydrophobic coating is stretched unilaterally to a length between about 110% to about 300% of its original length. In additional embodiments, the stretchable, hydrophobic materials retain at least 80% or 90% or 95% or 99% or all of their hydrophobicity after at least four abrasion cycles, and/or may exhibit a high fluid droplet mobility with a roll-off angle not greater than 20 degrees. In some embodiments, the stretchable, hydrophobic materials both retain their hydrophobicity as set forth above after at least four abrasion cycles and exhibit a high fluid droplet mobility with a roll-off angle not greater than 20 degrees.

Articles that are coated with a stretchable, hydrophobic material are also presented, including embodiments wherein the articles are personal protective equipment, such as a glove, or a bandage.

Embodiments of processes for rendering a stretchable surface hydrophobic are presented, by dispensing liquid polymer to a stretchable surface forming a layer of liquid polymer thereon, and embedding a plurality of hydrophobic particles into the layer of liquid polymer to form a hydrophobic surface. In some embodiments, the hydrophobic surface exhibits an increase in water contact angle when stretched unilaterally to a length between about 110% to about 300%, or about 150 to about 250%, or about 180% to about 220%, of its original length.

Additionally, processes for manufacturing a stretchable hydrophobic glove are presented, by dispensing liquid polymer to the outer surface of a stretchable glove forming a layer of liquid polymer thereon, applying a plurality of hydrophobic particles to the liquid layer of polymer such that at least a portion of the plurality of particles are embedded into the liquid layer of polymer, and drying the liquid layer of polymer.

In certain embodiments of these processes, the liquid polymer comprises latex, nitrile, or polydimethylsiloxane. In some embodiments, the substrate comprises latex and/or nitrile. In further embodiments, the hydrophobic particles comprise polytetrafluoroethylene or silica. For example, in some embodiments the hydrophobic particles comprise silica particles having a hydrophobic shell. In some embodiments, the hydrophobic particles comprise silica coated with hexamethyldisilazane or polydimethylsiloxane.

Further, coating compositions are presented, comprising a plurality of hydrophobic particles and a polymer, wherein at least a portion of the plurality of hydrophobic particles are embedded in the polymer, and wherein the compositions form a stretchable and hydrophobic coating. In some embodiments, the hydrophobic coating exhibits an increase in water contact angle when stretched. In certain embodiments, the hydrophobic coatings retain at least 80% or 90% or 95% or 99% or all of its hydrophobicity after at least four abrasion cycles. In an additional embodiment, the hydrophobic coating exhibits high fluid droplet mobility with a roll-off angle not greater than 20 degrees. In further embodiments, the hydrophobic coatings have one or more of the following characteristics: they exhibit an increase in water contact angle when stretched, they retain their hydrophobicity after at least four abrasion cycles, and they exhibit high fluid droplet mobility with a roll-off angle not greater than 20 degrees.

Additional coating compositions are presented comprising a plurality of hydrophobic particles comprising or consisting essentially of or consisting of a plurality of silica particles having a hexamethyldisilazane or polydimethylsiloxane shell, and latex or nitrile, wherein the compositions form a superhydrophobic and stretchable coating when applied to a substrate.

The foregoing and other objects, features, and advantages of the invention will become more apparent from the following detailed description, which proceeds with reference to the accompanying figures.

BRIEF DESCRIPTION OF THE DRAWINGS

Various embodiments are shown and described in connection with the following drawings.

FIG. 12 are SEM images of an unstretched (left) and stretched (right) exemplary stretchable hydrophobic material. The material was stretched linearly to 200% of its original length for the stretched images.

Figure 1:
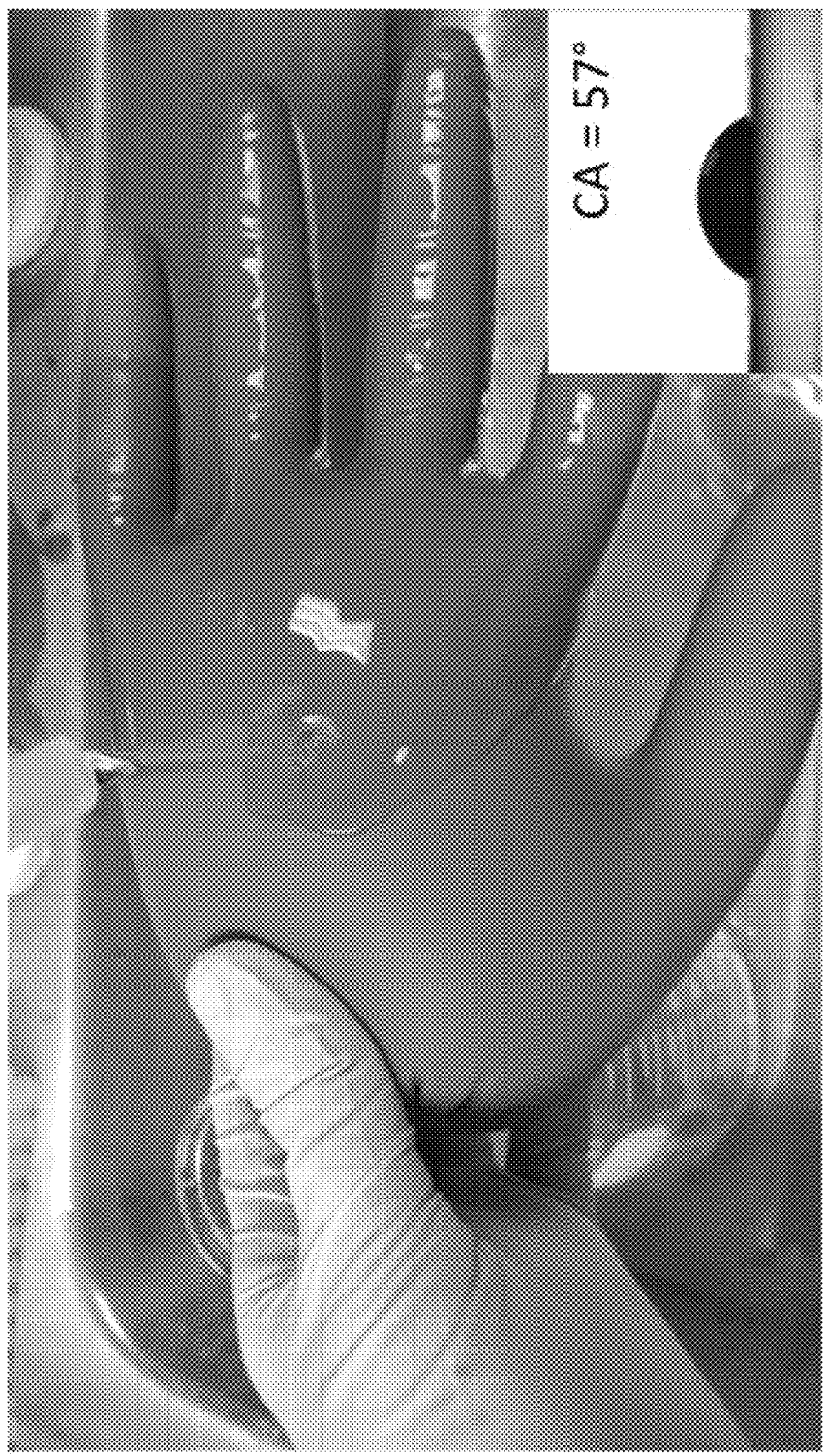
FIG. 1 is a photograph of a conventional nitrile glove that is not coated with a stretchable hydrophobic material, under a stream of water. The inset of FIG. 1 shows a photograph of a drop of water on the surface of the non-coated glove, with a contact angle of 57 degrees.

Cassie-Baxter state wetting over a stretching nanotextured surface is shown in the far right illustration.

DETAILED DESCRIPTION

The development of synthetic hydrophobic materials has been inspired by the self-cleaning and water repellent surfaces of plants such as the lotus (*N. nucifera*) or pitcher plants of the nepenthes genus. The wettability of such hydrophobic and slippery materials is usually determined by measuring its water contact angle (CA). Materials with a CA greater than 150 degrees are considered to be superhydrophobic, and the high CA causes water to form beads that roll off the surface even at very low angles. The mechanism of the so-called "lotus leaf effect" is drawn primarily from its surface structure, which consists of 10-20 μm protruding bumps with 70-100 nm sized fibers of epicuticular wax crystalloids. The micro/nanoscale hierarchical texture of the lotus leaf surface allows air to be trapped underneath droplets of liquid, reducing a liquid's ability to fully wet the surface.

PPE materials imparted with hydrophobic properties may reduce cross contamination and infection by eliminating uptake and transfer of infectious liquids. For example, it is estimated that about 27 billion disposable gloves are used globally each year, primarily in hospitals and medical settings, food preparation and service, chemical handling, and laboratory research. The majority of these gloves are used once and for a short period of time before disposal. Disposable gloves are relatively inexpensive yet their use limits the spread of diseases with expensive deleterious effects. However, glove safety depends on their proper use, which is subject to human error. As a result, hospital acquired infections are a persistent and expensive threat to human health.

The CDC estimates that roughly 10% of hospitalized patients will become infected with a hospital acquired infection, and these infections cause or contribute to 99,000 deaths annually in the US. The annual costs associated with hospital infections are estimated to be $4.5-11 billion per year. In many cases, the risks of transfer of infectious material could be reduced through the use of gloves with improved hydrophobic properties. Even a moderate reduction of hospital acquired infections would provide substantial economic benefit.

Artificial hydrophobic surfaces have been synthesized by a variety of methods that follow top down approaches, bottom up approaches, or a combination of these approaches. However, conventional synthetic hydrophobic materials generally have limited durability, and also cannot be applied to flexible and stretchable materials such as gloves and textiles because they are rigid and inflexible.

The materials and methods disclosed herein address the limited durability and inflexibility of conventional synthetic hydrophobic materials. Specifically, methods to fabricate a stretchable and durable hydrophobic material that can be integrated into a variety of articles, such as PPE and including disposable gloves, are described. The methods used to make embodiments of the stretchable hydrophobic materials described herein may be readily applied to single-use disposable gloves in an efficient and inexpensive manner. Conventional sterile exam and surgical gloves currently cost between $0.03-0.50 each, and it is estimated that it would cost approximately $0.10-0.15, and maybe less, to implement the described technology. Embodiments of the present disclosure can be implemented on a commercial scale. Further, embodiments of the stretchable hydrophobic material can also be integrated into any article that could benefit from protection from water, or any moisture, such as apparel, tents, umbrellas, and like items.

I. TERMS

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, properties such as contact angles, percentages, and so forth, as used in the specification or claims are to be understood as being modified by the term "about." Accordingly, unless otherwise implicitly or explicitly indicated, or unless the context if properly understood by a person of ordinary skill in the art to have a more definitive construction, non-numerical properties such as flexible, continuous, homogeneous, and so forth as used in the specification or claims are to be understood as being modified by the term "substantially," meaning to a great extent or degree. Accordingly, unless otherwise indicated, implicitly or explicitly, the numerical parameters and/or non-numerical properties set forth are approximations that may depend on the desired properties sought, limits of detection under standard test conditions/methods, limitations of the processing method, and/or the nature of the parameter or property. When directly and explicitly distinguishing embodiments from discussed prior art, the embodiment numbers are not approximates unless the word "about" is recited.

In order to facilitate review of the various embodiments of the disclosure, the following explanations of specific terms are provided:

The term "flexible" as used herein refers to a material that can bend without breaking, and which returns essentially unchanged to its original size after flexing.

As used herein, the term "hydrophobic material" refers to a solid material that repels water on its surface. A drop of water on the surface of a hydrophobic material will minimize its contact with the surface and instead form a compact droplet to avoid contact with the surface. A hydrophobic material exhibits a water contact angle that is greater than or equal to 90 degrees. A "superhydrophobic material" as used herein, refers to a hydrophobic material that exhibits a water contact angle greater than or equal to 150 degrees. The water contact angles were measured by drop shape analysis of sessile water droplets using a goniometer.

Although hydrophobicity refers specifically to water, the stretchable hydrophobic materials disclosed herein also repel liquids including biological fluids, such as blood or urine. Herein, the terms "hydrophobic coating" and "hydrophobic material" are used interchangeably unless context clearly indicated otherwise. Some embodiments of the materials disclosed herein are omniphobic and/or oleophobic in addition to being hydrophobic, as indicated.

As used herein, the term "latex" refers to a dispersion of latex polymer in an aqueous medium. The latex can be from natural sources or can be synthetically prepared. As used herein, the term "liquid latex" refers to wet latex. Liquid latex allows particles to become permanently embedded into the latex.

The term "layer" as used herein refers to a substantially continuous sheet of a material on a surface. For example, a stretchable hydrophobic coating may form a layer on a substrate which covers at least 70% of the exposed surface of the substrate, at least 80% of the exposed surface of the substrate, or at least 90% of the exposed surface of the substrate.

The term "shell" as used herein refers to an outer layer of material that encapsulates a particle. In an embodiment, particles are partially or substantially encompassed by the shell, for example, the particle surface may be at least 50% encompassed by the shell, at least 60% encompassed, at least 70% encompassed, at least 80% encompassed, at least 90% encompassed, or may be about 100% encompassed.

In certain embodiments, the shell comprises an organosilicon compound including polydimethylsiloxane (PDMS), a silazane or a siloxane, a fluoropolymer including polytetrafluoroethylene (PTFE), a fluorinated silicone, or a combination thereof. In some embodiments, the shell comprises hexamethyldisilazane (HMDS) or PDMS. In certain embodiments, the shell is a hydrophobic shell.

As used herein, the term "stretchable" refers to the property of a coating or material to extend in at least one direction beyond its original size and return to its original size with no significant loss of its structural integrity. The coating or material is able to be stretched easily, that is, manually. In some embodiments, the materials disclosed herein retain their hydrophobicity when stretched.

In certain embodiments, a stretchable material can be extended unilaterally to at least 110% of its original length, meaning that it stretches to a length that is at least an additional 10% longer than its original length, or 1.1 times its original length, with no significant loss of its structural integrity. For example, a stretchable material can be extended from about 110% to about 200% of its original length, or from about 110% to about 175% or is original length, or from about 110% to about 400% of its original length, with no significant loss of its structural integrity. In other embodiments, a stretchable material can be extended from about 1.1 to about 2.0 times its original length, or from about 1.1 to about 1.75 times its original length, or from about 1.1 to about 4.0 times its original length, with no significant loss of its structural integrity. In an embodiment, the stretchable material exhibits a measurable increase in its hydrophobicity when stretched.

In further embodiments, a stretchable material changes in length by no more than about 20% after being stretched to about 300% of its original length and allowed to relax. In some embodiments, a stretchable material changes in length by no more than about 10% after being stretched to about 300% of its original length and allowed to relax. In certain embodiments, a stretchable material changes in length by no more than about 5% after being stretched to 300% of its original length and allowed to relax.

In additional embodiments, a stretchable material has a Young's modulus of less than about 2 gigapascal. In some embodiments, a stretchable material has a Young's modulus of less than about 1.5 gigapascal. In certain embodiments, a stretchable material has a Young's modulus of less than about 1 gigapascal. In further embodiments, a stretchable material has a Young's modulus between about 0.01 and about 3 gigapascal.

The term "substrate" as used herein, refers to the surface onto which the hydrophobic materials described herein may be delivered, applied, or introduced and are in direct physical contact with the hydrophobic materials. Substrates suitable for use include materials such as latex and nitrile rubber, silicones, textiles such as cotton and canvas, composite materials such as fiberglass, fluoropolymers, concrete, wood, fibrous materials, polymeric materials, wicking materials such as fiberglass weaves, bandages, glass, steel, painted surfaces, automobiles, coated surfaces, and other selected materials including combinations of these surfaces, materials, and substrates. For example, the stretchable hydrophobic coating compositions described herein may be applied to substantially any substrate, stretchable or not stretchable, to form a hydrophobic layer thereon. It should be noted that not all substrate materials are considered equivalent to the others for purposes of this disclosure and its embodiments.

The terms "wettable" and "wettability" refer to the ability of a liquid to maintain contact with a solid surface. For a hydrophobic surface, the wetting of the surface is unfavorable and the surface is considered to have low wettability, as the liquid has little contact with the surface. In contrast, for a hydrophilic surface, a water droplet will spread out on the surface and wetting is favorable, as the surface is considered to have high wettability with a large amount of contact between the liquid and the surface. A surface having a water contact angle of zero degrees is perfectly wetting, and a surface having a contact angle of 180 degrees is perfectly non-wetting. Thus, the water contact angle is an inverse measure of wettability.

II. STRETCHABLE HYDROPHOBIC MATERIALS

Certain embodiments of the stretchable hydrophobic materials disclosed herein are comprised of a plurality of hydrophobic particles embedded into a polymer. The hydrophobic particles may be made of a single hydrophobic component, such as PDMS or PTFE. Alternatively, the hydrophobic particles may be formed from multiple components, such as a core material encompassed by a hydrophobic shell. The hydrophobic particles may be made of a non-hydrophobic core material and coated with a hydrophobic shell, or they may be made of a hydrophobic core material which may or may not be coated with an additional hydrophobic shell.

The stretchable hydrophobic material may be used as a coating for an article or a substrate. The coating may be made with a plurality of hydrophobic particles and a polymer, wherein at least a portion of the plurality of the hydrophobic particles are embedded in the polymer. In certain embodiments, the coating is superhydrophobic.

In an embodiment, the hydrophobic particles are particles of fumed silica coated with a hydrophobic shell. Fumed silica is used as an additive in many composites and emulsions, including in foods, cosmetics, and toothpaste, and is generally considered nontoxic. The average size of the silica particles may be between about 1 and about 200 nm, with an average surface area of between about 1 and about 600 $m^2/g$.

In some embodiments, the silica particles are coated with a hydrophobic shell which partially or completely encompasses the particles. In one embodiment, the shell comprises HMDS or PDMS. Silica particles coated with a shell comprising a compound other than HMDS may also be used to render the particles hydrophobic, such as PDMS, PTFE, other organo silazanes, silanes and organosilanes. In certain embodiments, the shell comprises an organo silazane, an organosilane including propyl silane, phenyl silane and t-butyl silane, a fluoropolymer including PTFE, a fluorinated silicone, or a combination thereof. In certain embodiments, the shell comprises an organosilane with the fomula R-silane wherein R is a carbon chain of 1 to 36 carbons, which optionally may be fluorinated. In some embodiments, the organosilane is a substituted phenyl silane which may optionally be fluorinated. It should be noted that not all shell compounds listed are considered equivalent to the others for purposes of this disclosure and its embodiments.

In some embodiments, particles other than silica are utilized. For example, titanic, ceramic particles, polystyrene or latex having a similar size as the silica may be amenable to surface modification with a hydrophobic shell. In certain embodiments, the hydrophobic particles are made of PTFE and have no shell.

The surface chemistry of the hydrophobic particle can affect particle stability, compatibility with the coating process, its effective dispersion during deposition and in the coating, and the hydrophobicity of the surface and its ability to shed liquids. Silica particles comprising an HMDS shell may be considered to have a molecular surface passivation layer on the silica and change its surface chemistry from polar to nonpolar-lipophilic. In certain embodiments, these composite particles exhibit improved dispersion into organic solvents that can lead to improved deposition, they are less prone to clumping on the substrate surface providing improved uniformity, and their nonpolar-lipophilic surface may provide improved roll-off of aqueous/polar and biological solutions.

The surface chemistry of the particles can be modified using covalent bonding, ionic bonding, physical sorption, and chemical coating. For example, silanization can modify ceramic surfaces such as silica and alumina, as well as metal and metal oxide surfaces, via gas or liquid treatment of the particles. Coating methods with physi-sorbed modifiers (oils, waxes, organics, fluorocarbons, etc.) can be relatively simple, such as by rinsing the particle in a liquid of interest. For example, organic oils can spread across surfaces of particles on contact and a surface coating may remain after their removal. In other cases, temperatures may require some control, such as for coating with waxes where warming and cooling may be needed for applying a surface coating. Coating particles with a shell of different material can impart the particles with hydrophobicity and/or with additional advantageous properties, such as improved dispersion and stability in a solvent.

The hydrophobic particles may be spherical but may also have other shapes. For example, in certain embodiments, the hydrophobic particles are tubular or fibrous. In an embodiment, the hydrophobic particles have an average diameter (or average mean longest dimension) between 1 nm and 200 micron. In further embodiments, the hydrophobic particles have an average diameter (or average mean longest dimension) between 15 nm and 500 nm, such as between 10 nm and 300 nm. In some embodiments, the hydrophobic particles are spherical.

The polymer of the stretchable hydrophobic material may comprise latex, nitrile, acrylate, methacrylate, polypropylene, polyethylene, PDMS, or any combination thereof. In an embodiment, the polymer comprises latex, nitrile or PDMS. The polymer may be a liquid polymer. In one embodiment, the polymer comprises liquid latex, liquid nitrile or liquid PDMS.

The thickness of the polymer may vary due to the size of the hydrophobic particles embedded therein. The minimum thickness is about half the average size of the hydrophobic particles. In an embodiment, the polymer has a minimum thickness of 25 nm and a maximum thickness of 1-2 mm.

The density of the hydrophobic particles in the polymer can be measured in multiple ways. For example, the particle density can be measured by counting the number of particles in a small area of an AFM image. In certain embodiments, the number of particles is between 0.01 and 1,000,000 per square micron. In some embodiments, the density is between 0.1 and 10,000 per square micron, or between 1 and 1000 per square. For example, the density can be about 85 particles per pmt. Particle density can also be measured by weighing the mass of particles applied to a sample of a given area using a typical spray procedure. In certain embodiments, the mass density of the particles is between 0.1 and 100 $g/m^2$. In some embodiments, the mass density of the particles is between 1 and 50 $g/m^2$, or about 7.5 $g/m^2$.

The polymer may be layered on a substrate, which itself may or may not be polymeric. The substrate may be hydrophobic or hydrophilic. In an embodiment, the substrate comprises latex, nitrile, or a combination of latex and nitrile. In some embodiments, the substrate is a latex and/or nitrile glove, or bandage material. The substrate may be a mold that forms a desired shape for the hydrophobic material, for example, a glove mold that is in the shape of a hand.

FIG. 1 is a photograph of a conventional disposable nitrile glove under a stream of water, getting wet. The water contact angle of this non-coated glove (inset of FIG. 1) shows a contact angle of 57 degrees, indicating that the glove is not hydrophobic.

Figure 2:
FIG. 2 is photograph of a nitrile glove coated with an exemplary stretchable hydrophobic material, under a stream of water. The inset of FIG. 2 shows a photograph of a drop of water on the surface of the coated glove, with a contact angle of 156 degrees.

FIG. 2 is a photograph of a nitrile glove coated with a stretchable hydrophobic material as disclosed herein in Example 1, under a stream of water. The water is rolling off the coated glove, as the glove has a contact angle of 156 degrees (inset of FIG. 2). Articles with a modified wetting behavior can shed liquids. A superhydrophobic surface, such as the one shown in FIG. 2, has a very high water contact angle and water forms beads that easily roll off of the surface. A stable protective layer of air forms around the glove as the water streams over it.

Figure 3:
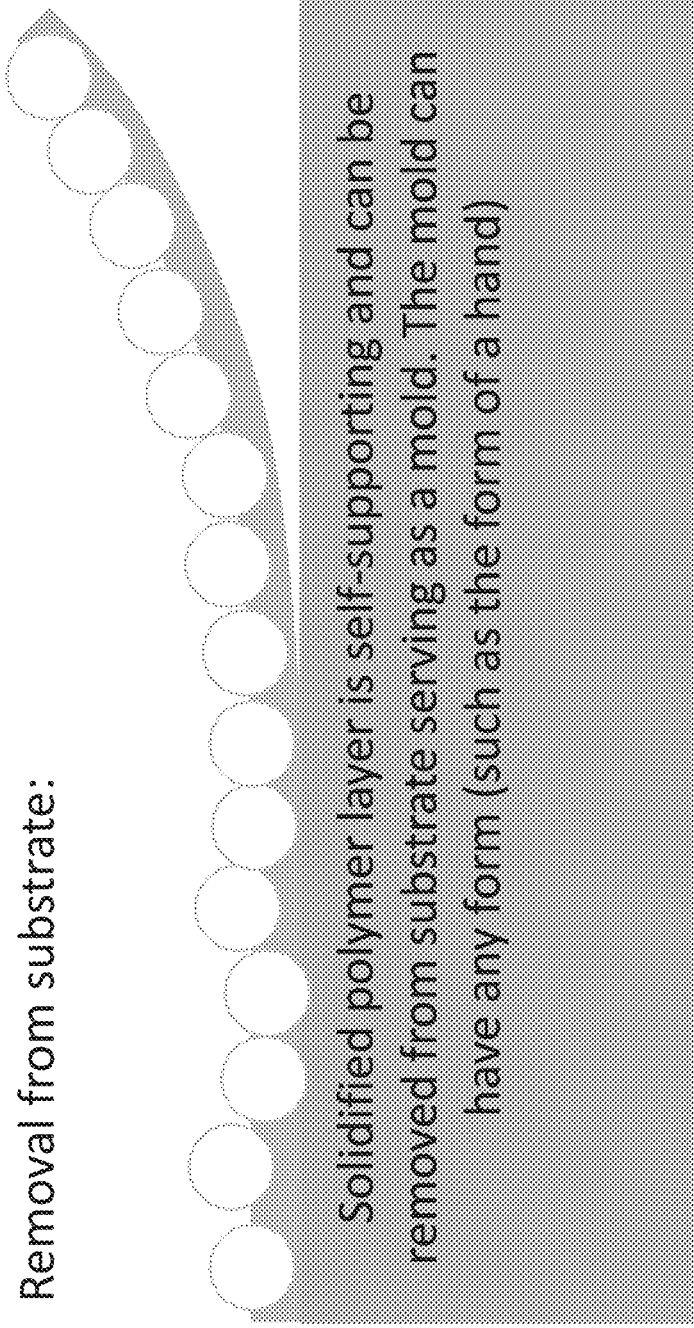
FIG. 3 is a schematic illustration showing in a certain embodiment, the stretchable hydrophobic material peeled away from a substrate to form a free-standing sheet or coating.

Alternatively, the polymer of the stretchable hydrophobic material may be a free-standing sheet of material. Such a free-standing sheet of material may be made, for example, by applying the polymer and hydrophobic particles to a glass substrate, and then peeling the dry stretchable hydrophobic coating away from the glass. FIG. 3 is a schematic illustration showing how, in certain embodiments, a stretchable hydrophobic material may be peeled away from a substrate to form a free-standing sheet or coating. In an embodiment, the free-standing material is formed in or on a mold and peeled therefrom.

The silica particles of the stretchable hydrophobic materials disclosed herein are embedded in the polymer, some partially and some completely embedded. The silica particles can aggregate within the polymer to form silica fibers. Non-silica particles can similarly form fibrous aggregates. When dry, the polymer secures these fibers and forms a hydrophobic material that is stretchable and durable. In certain embodiments, the stretchable hydrophobic materials remain hydrophobic when stretched to over 100% or 200% or 300% of their original length. In certain embodiments, the stretchable hydrophobic materials remain hydrophobic with repeated cycles of stretching and relaxation (100 or more cycles), and when challenged with aggressive abrasion.

Figure 4:
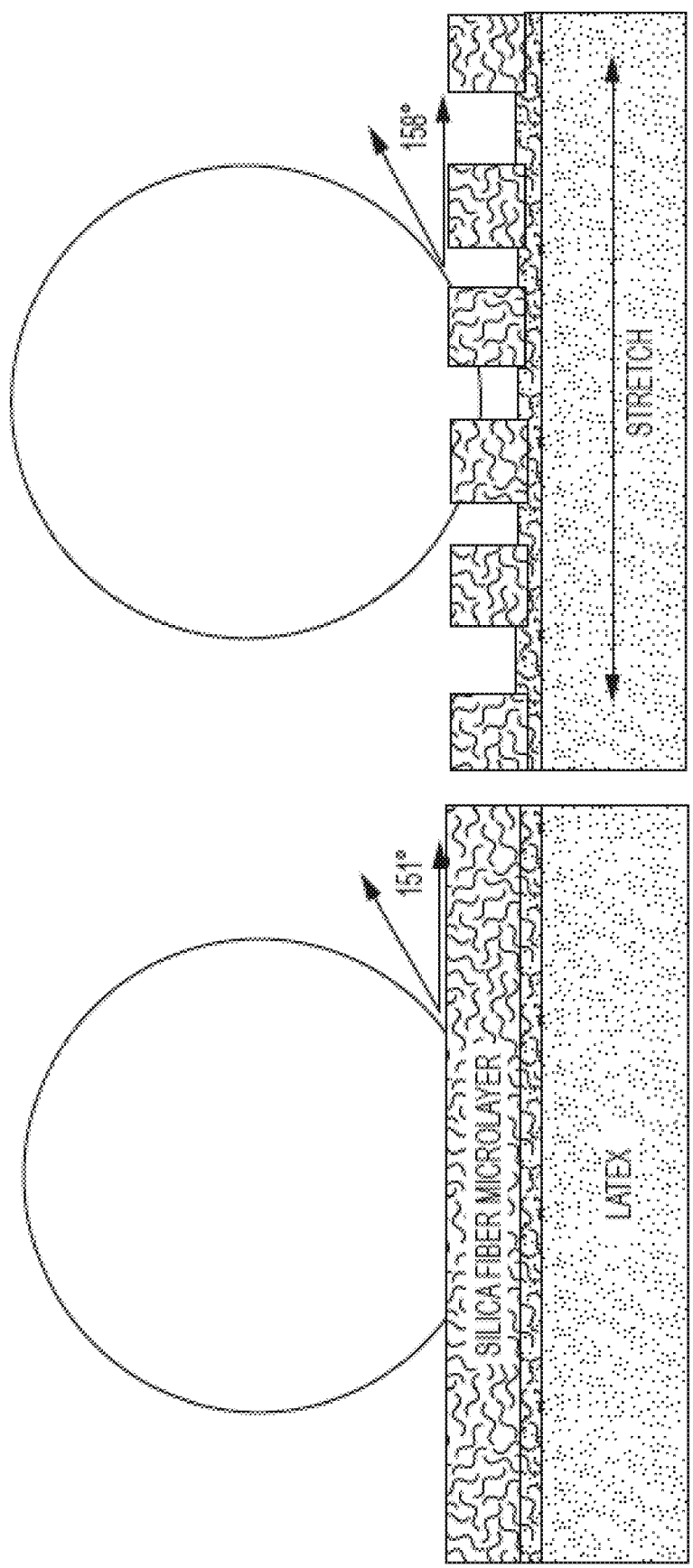
FIG. 4 is an illustration of a water droplet on an unstretched (left illustration, with a contact angle of 151 degrees) and a stretched (right illustration, with a contact angle of 158 degrees) exemplary stretchable hydrophobic material, showing how in certain embodiments, the material may increase its hydrophobicity when stretched.

In fact, it was surprisingly discovered that the unique structure of some embodiments of the stretchable hydrophobic materials disclosed herein result in their becoming more hydrophobic as they are stretched. This is shown in FIG. 4. This result is counter-intuitive because external stress usually leads to a decline in hydrophobicity in textured materials. Changing the texture by moving or removing certain features of a conventional hydrophobic material can result in a significant decline in contact angle. It was expected that stretching the coating would cause the dense layer of particles at the surface to crack, disintegrate, or separate from the underlying polymer and that this would cause the underlying polymer to be exposed and more susceptible to wetting. Instead, it was found that the scale, separation and orientation of microscale and nanoscale features can be carefully controlled to create a hydrophobic material.

FIG. 4 is a schematic illustration of how certain embodiments of the stretchable hydrophobic materials can increase their hydrophobicity when stretched. The illustration on the left side of FIG. 4 shows a water droplet with a contact angle of 151 degrees on a silica fiber microlayer on a latex substrate. A feature of this layer is that it has a relatively homogenous nanostructured surface. In contrast to the natural lotus leaf, this layer does not have a hierarchical structure. It lacks micron-sized features.

When the latex substrate is stretched in the directions of the arrows shown in the right side of FIG. 4, the silica layer spontaneously forms microscale islands of the silica fibers, and the water droplet has a higher contact angle of 158 degrees. The spontaneous formation of microscale features at the surface of the coating leads to a transition from a surface with only nanostructured features to a surface with both nano- and micro-sized features. Surfaces with mixed nano- and micro-sized features generally have higher contact angles than those with exclusively nano- or micro-sized features. The result observed for this material was particularly surprising because although the surface did crack upon stretching, rather than exposing the underlying polymer to wetting, the cracks formed micro-sized features. The emergence of these micro-sized features caused the surface to instead repel water, and resulted in its having a large contact angle and low wettability.

When such a hydrophobic material is applied to a stretchable substrate such as gloves, the gloves remain dry (that is, they retain their hydrophobicity) when they come into contact with fluids such as water (see, e.g., FIG. 2) and biological fluids such as blood. Certain embodiments of the stretchable hydrophobic materials address the problem of conventional hydrophobic materials lacking long term durability. It was unexpectedly found that when an embodiment of the stretchable hydrophobic coatings was applied to a latex glove, the stretchable latex substrate allowed for the surface-attached silica particles, and silica fibers made therefrom, to flex rather than shear under pressure or abrasion. By allowing the hydrophobic nanofibers to bend with the underlying polymer rather than shearing off, the bonding and thus durability of the stretchable hydrophobic materials can remain strong over time. Strongly bonded nanofibers can prevent exposure of underlying materials with lower hydrophobicity or hydrophilicity.

In certain embodiments, the stretchable hydrophobic materials are nontoxic. In an embodiment, the stretchable hydrophobic material is a superhydrophobic material.

Embodiments of the stretchable hydrophobic materials disclosed herein can be used for apparel and other articles, including PPE. These articles cannot be completely wetted by fluids such as water and biological fluids such as blood. Instead, liquids form beads on the surface of the article and simply roll off. Certain embodiments of the stretchable hydrophobic materials resist abrasion and thus, can maintain their hydrophobicity during active use. In an embodiment, the stretchable hydrophobic materials increase their hydrophobicity when stretched beyond their original size.

For example, PPE such as suits made from Tyvek, boots or aprons made from rubber, head coverings or splash guards, can be coated with, or integrate, certain embodiments of the stretchable hydrophobic materials. In addition, there are potential applications in the healthcare field to protect medical devices, walls, or bedding from contaminating liquids. In the food preparation and food service industries, embodiments of the stretchable hydrophobic materials could be used to coat surfaces that physically contact food. Industrial and scientific research involving biomaterials and/or hazardous chemicals can use the disclosed hydrophobic materials to reduce contamination when transferring liquids in pipets, beakers or tubing. The stretchable nature of some embodiments of the stretchable hydrophobic materials may be particularly useful to coat tubing. For example, a latex polymer can stick to glassware but can be removed and reapplied when desired, for embodiments where peelable and/or temporary stretchable hydrophobic coatings may be useful.

Embodiments of the stretchable hydrophobic materials described herein may be applied to other single use disposable items such as cardboard boxes or Tyvek envelopes, for protection from external liquids or to contain spilled liquids. Selected application of the materials could be used to direct the flow of liquids in a desired direction. In some embodiments, free-standing films of the stretchable hydrophobic materials could be stretched to fit over large or irregular objects when temporary protection from moisture is desired. Such materials could be used to protect sensitive electronics from water damage. In certain embodiments, the stretchable hydrophobic materials are nonconductive and could be used to encase or coat the interior of cell phones, laptops, cameras, or other electronic articles. Once applied, embodiments of the stretchable hydrophobic materials can stretch or be easily peeled away if needed. Embodiments of the stretchable hydrophobic materials may be used to make ordinary objects such as paper or thin plastic into highly effective temporary rain protection, similar to an umbrella, tent or disposable rain coat. Embodiments of the stretchable hydrophobic materials may be used to impart ordinary objects like cardboard boxes with effective protection against water or rain.

In certain embodiments, the stretchable hydrophobic materials provide a good gripping surface and/or are durable against moderate abrasion. Any article that may become slippery when wet may be coated with this material to remain dry and allow a proper grip, such as handles, floors or floor coverings, cooking utensils, or gripping bars in the shower or bathroom. In addition to gloves and other PPE, the stretchable hydrophobic materials could have a number of other applications including bandages, masks and packing materials. Embodiments of these coatings can be applied to 3-D structures and textured surfaces such as gloves, cloths, wools, knurled metals, cardboard, paperboard, gypsum board, molded plastic or rubber. Application of these coatings to 3-D structures will allow the structures to shed liquids which are contacted, captured or condensed on the surfaces, or be applied to the borders or external portions of a diaper or absorbent pad. In certain embodiments, the stretchable hydrophobic materials can be used on gently sloping outdoor walkways or paths in rainy or moist areas, such as around water features or pools, including on concrete.

In addition, certain embodiments of the stretchable hydrophobic materials may be useful for medical bandages, casts or wrapping that will not allow liquids to pass through them. For example, bandages which incorporate stretchable hydrophobic materials could keep wounds dry and clean but allow patients to wash and shower. The stretchable hydrophobic materials may be applied to all or a portion of a microfluidic device, a flexible electronic, a medical implant, a catheter, a tube, a bottle. The materials could be applied to a manned or unmanned aerial vehicle or drone, allowing it to fly in inclement weather without the negative effects of water accumulation on electronic components or propellers. Some embodiments of the stretchable hydrophobic materials described herein could be made into balloons. The balloons could be released into the atmosphere to make measurements of weather or climate conditions without accumulating moisture. In addition, embodiments of this invention could be used to prevent the accumulation of ice on high altitude balloons and/or their payloads.

III. METHODS OF MAKING HYDROPHOBIC MATERIALS

This disclosure provides embodiments of efficient processes to provide stretchable and durable coatings to impart articles, such as bandages and gloves, with hydrophobic properties. The stretchable hydrophobic materials are comprised of hydrophobic particles which are embedded into a polymer. In certain embodiments, the polymer is a liquid polymer, which can be applied to the surface of an article to form a layer of liquid polymer. A plurality of hydrophobic particles can be applied to the liquid polymer layer. In certain embodiments, the hydrophobic particles have a hydrophobic shell encasing them. The hydrophobic particles can aggregate within or on the surface of the polymer to form a densely packed hydrophobic nanostructured layer. When the liquid polymer dries, it can secure this packed nanostructured layer to form a stretchable hydrophobic material.

Generally, a stretchable surface may be rendered hydrophobic by dispensing or otherwise applying liquid polymer to the surface forming a layer of liquid polymer thereon and embedding a plurality of hydrophobic particles into the layer of liquid polymer to form the hydrophobic surface. The hydrophobic surface may be the surface of a PPE, such as a glove. A stretchable hydrophobic glove may be manufactured on a commercial/industrial scale by dispensing liquid polymer to the outer surface of the glove, forming a layer of liquid polymer thereon and introducing a plurality of hydrophobic particles into the liquid layer of polymer such that at least a portion of the plurality of particles are embedded into the liquid layer of polymer. The liquid layer of polymer may then be dried or may be allowed to solidify without further action performed.

The hydrophobic particles are embedded into the liquid polymer. In certain embodiments, the dwell time between when the liquid polymer is applied to a substrate and when the particles are applied to the liquid polymer is not greater than about 10 minutes, not greater than about 5 minutes, not greater than about 4 minutes, not greater than about 3 minutes, not greater than about 4 minutes, or not greater than about 1 minute. In some embodiments, the particles are applied to the liquid polymer within about 10 minutes after the liquid polymer is applied to a substrate, within about 5 minutes after the liquid polymer is applied to a substrate, within about 4 minutes after the liquid polymer is applied to a substrate, within about 3 minutes after the liquid polymer is applied to a substrate, within about 2 minutes after the liquid polymer is applied to a substrate, or within about 1 minute after the liquid polymer is applied to a substrate. The liquid polymer may be, for example, liquid latex, liquid nitrile or liquid polydimethylsiloxane.

The stretchable hydrophobic material may be incorporated into an article, such as a glove, or it may be applied to the surface of an article or other substrate. The surface onto which the hydrophobic materials described herein may be applied include polymeric materials such as gloves, textiles including fabric bandages, and non-stretchable materials such as concrete. In fact, the stretchable hydrophobic coating compositions described herein may be applied to substantially any substrate to form a hydrophobic layer thereon.

In surgical settings, the use of natural latex gloves is preferred despite allergenic concerns, because they can be made thin and defect free, which provides protection without sacrificing a fine sense of touch for the user. In an embodiment, hydrophobic silica particles were integrated with latex in order that the resulting coated gloves would have similar properties to conventional non-coated gloves, except with a more hydrophobic surface. It was found that making a composite mixture of hydrophobic silica particles with water based latex emulsions was not feasible due to the inability of the two components to physically mix. Instead, a multistep process to make stretchable hydrophobic material was developed.

Figure 5:
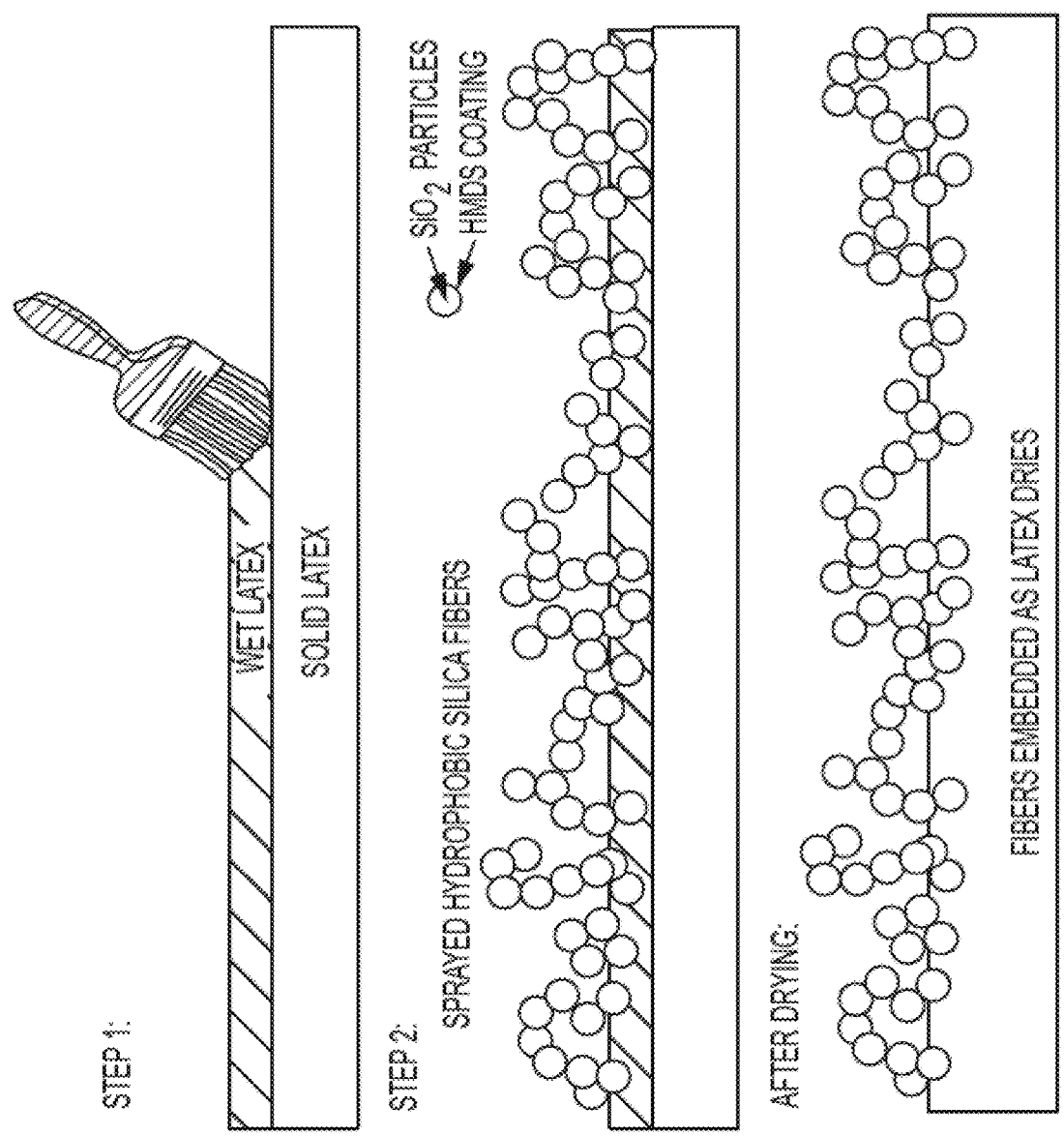
FIG. 5 is an illustration of an exemplary process to apply an embodiment of a stretchable hydrophobic material to a latex substrate.

FIG. 5 is an illustration of an embodiment of a multistep process that may be used to apply a stretchable hydrophobic coating to a dry latex substrate. As shown in FIG. 5, liquid latex was applied to the substrate surface as a liquid emulsion in a manner similar to a conventional industrial glove-making process. Then while the liquid latex was still wet, this surface was sprayed with a thin layer of densely packed hydrophobic silica particles.

In the exemplary fabrication process for creating an embodiment of a stretchable hydrophobic coating integral to a thin latex film shown in FIG. 5, a layer of liquid latex is applied over a dry latex substrate. While the applied latex layer is still a liquid, silica particles comprising a hydrophobic shell of HMDS were sprayed onto the layer of liquid latex to form a dense microlayer of embedded particles. The application may be made by a variety of techniques, including painting, dip coating, spraying with an airbrush, or electrostatic methods. The force used to apply the particles to the applied liquid polymer layer may vary depending upon the particle application technique used, which may also affect the density of particle embedding.

Figure 6:
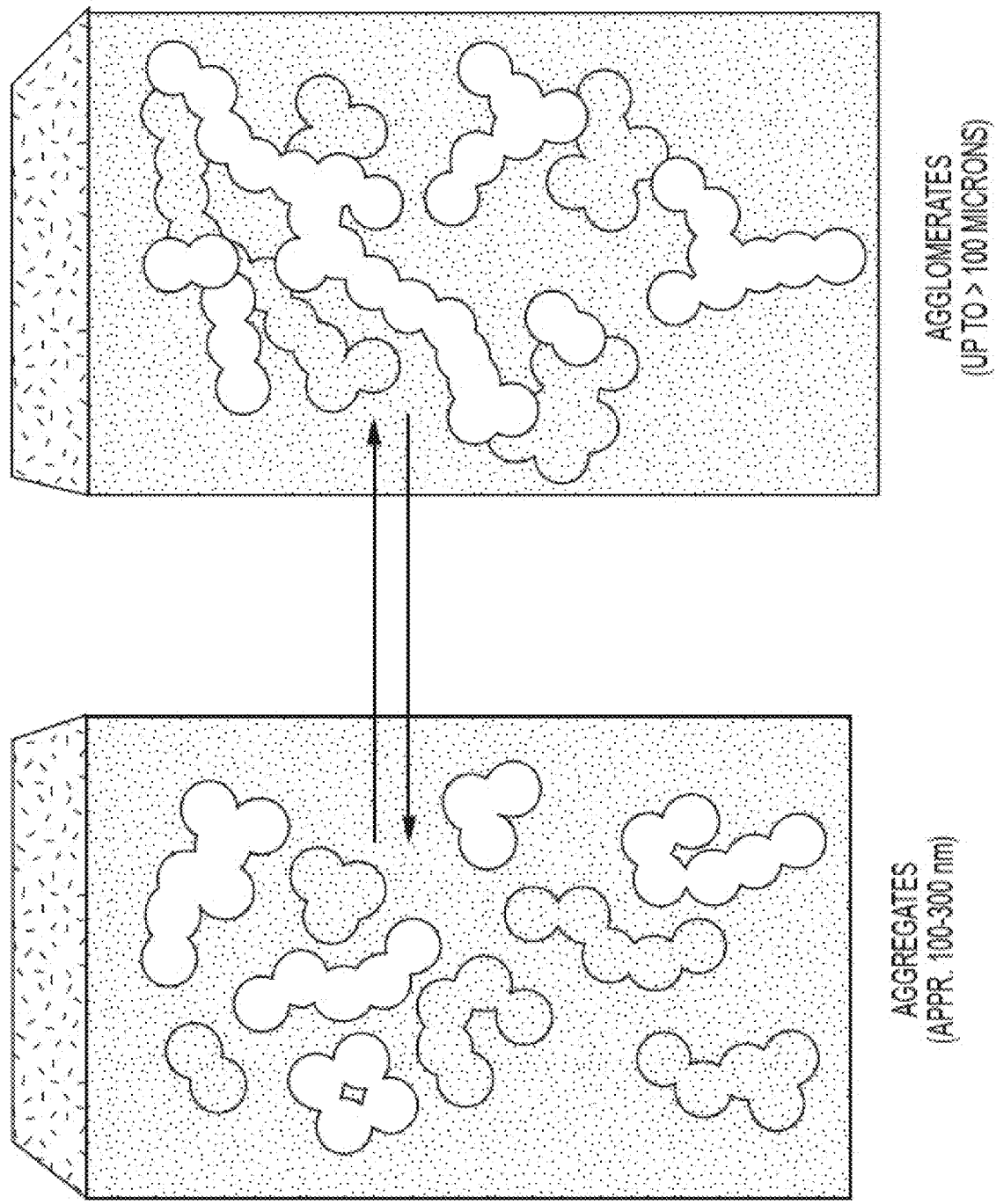
FIG. 6 is a schematic illustration of exemplary hydrophobic particle aggregating into fibers (left illustration), and further agglomeration into larger chains (right illustration).

FIG. 6 shows aggregation of the hydrophobic particles into fibers, and also further agglomeration into larger chains. The silica particles with a hydrophobic shell have an average diameter of between about 10 nm and about 150 nm. These particles can aggregate into silica fibers, with a typical fiber length being between about 100 nm to about 300 nm. The fibers then form larger agglomerates that can exceed 10 µm in length. Small particle size helps to impart hydrophobicity to the material. Intermediate chains and larger agglomerates contribute to the material's stability as well as to the formation of microtexture that enhances the material's hydrophobicity. As noted, the particles that make up the fibers can be encased within a hydrophobic shell, or may themselves be hydrophobic. As the applied liquid polymer dries, the fibers become embedded in the liquid polymer and the coating becomes hydrophobic.

Figure 7:
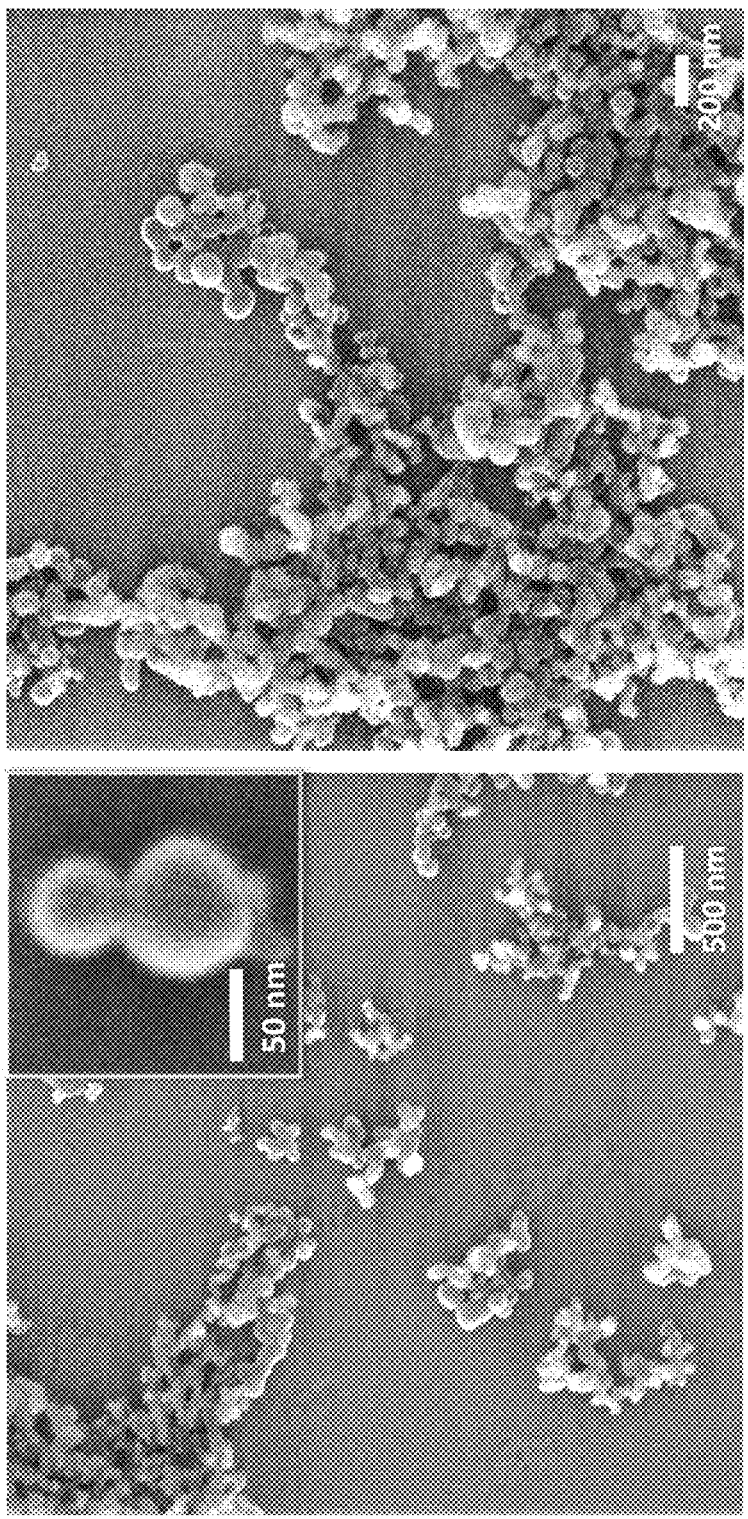
FIG. 7 is helium ion microscopy images showing the morphology of exemplary particles of silica coated with hexamethyldisilazane (HMDS) in an embodiment of a stretchable hydrophobic material. The left, right, and inset images show varying magnifications of primary particles of 20-150 nm and chains and agglomerates of 100-1000 nm.

FIG. 7 is a series of helium ion microscopy images showing the morphology of particles of fumed silica coated with HMDS, with the left, right, and inset images show varying magnifications. The images indicate that the primary particle size is 20-150 nm and that the chains and agglomerates are 100-1000 nm in length.

In certain embodiments, the hydrophobic particle size ranges between 1 nm and 200 nm, and the chains and agglomerates range between 200 nm and 10 micron.

The hydrophobic particles are applied to the substrate surface without waiting for the applied liquid polymer to dry, as indicated in step 2 of FIG. 5. One method to get durable adhesion of the hydrophobic particles to water-based liquid polymer is via aerosol application of the particles. The dry particles may be mixed into a volatile solvent, such as hexane, prior to application with an airbrush.

It was found to be useful to mix the particles with a solvent in a ratio that allowed for complete or almost complete evaporation of the solvent before reaching the polymer surface. For example, the ratio of solvent to particles by weight may range between about 10:1 and 4:1. In certain embodiments, the ratio of solvent to particles is about 6:1. In certain embodiments, the application of the hydrophobic particles to the liquid polymer is made by painting, dip coating, or spraying.

As indicated in the last two steps of FIG. 5, the fibers can then form an even coating and become embedded into the wet layer of applied polymer. Then as the liquid polymer dries, the hydrophobic particles form a durable coating having a layer of well-attached fibers on its outer surface.

The density of the particles in the polymer may be adjusted to control the amount of hydrophobicity of the stretchable hydrophobic materials. In an embodiment, the particle density is approximately 85 particles per pmt or the mass density of the particles is approximately 7.5 g/m$^2$.

The applied liquid polymer can comprise latex, nitrile or PDMS. In some embodiments the liquid polymer is a mixture of one or more of the listed polymers. The liquid polymer can be applied to a substrate that comprises latex and/or nitrile. In certain embodiments, both the liquid polymer and the substrate comprise latex. In some embodiments, both the liquid polymer and the substrate comprise nitrile. In an embodiment, the liquid polymer comprises latex, nitrile or PDMS, and the substrate comprises a non-polymeric material. The hydrophobic particles may comprise silica or PTFE, and may comprise silica coated with a hydrophobic shell of HMDS or PDMS.

Embodiments of the processes for making the stretchable hydrophobic materials are amenable for coating a stretchable substrate, which can be used to impart hydrophobic properties to fabrics and other articles that would benefit from a stretchable coating that sheds liquid.

IV. EXAMPLES

Materials. Latex sheets (Super-Stretchable Abrasion-Resistant Natural Rubber Sheets) were purchased from McMaster-Carr, with a thickness of from 0.006 inches to 0.030 inches. Latex gloves (Bio-Shield Plus Latex Powder Free Examination Gloves) were purchased from Bio-Flex. Nitrile gloves (KC500 Purple Nitrile-Xtra Powder-Free Exam Gloves) were purchased from Kimberly-Clark. For tests with nitrile sheets, sections of nitrile were cut from flat portions of nitrile gloves. Tyvek® with Tychem® coating and Krytox 103 were purchased from DuPont. A lotus plant (*Nelumbo nucifera*) was purchased from a garden supply company in Richland, Wash. Leaves from the plant were cut fresh as needed for testing. PTFE sheets (Teflon®) sheets were purchased from McMaster-Carr. Liquid Latex (TAP Premium Liquid Latex Rubber) was purchased from TAP Plastics. Liquid nitrile (Nychem 2000) was obtained from Emerald Performance Materials, PDMS (Sylgard 182) was purchased from Dow Corning as a kit with base and curing agent. AU AEROSIL particles were purchased from Evonik. AEROSIL particles are fumed silica and some particles have shell coatings as indicated. An references to fumed silica with HMDS refer to AEROSIL RX-50 (except where otherwise indicated). PTFE Powders were purchased from Sigma-Aldrich. Silica spheres were purchased from Cospheric, LLC.

All solvents used to dilute particles, and calcium carbonate, were purchased from Sigma-Aldrich. Substrates were purchased as follows: Teflon®, polypropylene sheets, polyethylene tarp, fabric (100% cotton canvas), and stainless steel sheets were purchased from McMaster-Carr. Wood, cork, concrete, and sheets of SiC sandpaper were purchased from a local building supply company (Home Depot, Richland, Wash.). Glass slides were purchased from Fisher Scientific. Bandages (First-Aid Brand Adhesive Bandages: Flexible Fabric) were purchased from American White Cross.

Contact Angle and Roll-off Angle Testing. The wettability of the sample materials was characterized by measuring water contact angles (CA) and roll off angles (ROA) with 15 µl droplets of water. The higher the CA, the more the material will resist wetting and retention of residual liquid. The lower the ROA, the better the material will shed liquids. CA were measured with a Ramé-Hart Model 500 goniometer. Samples were laid flat on the imaging platform and leveled in all directions. The liquid dispensing syringe was used to dispense 15 µl of deionized water to the sample. DropImage Advanced software was used to take images of the drop shape and calculate the contact angle. Averages from 10 images were collected every 0.5 seconds, and reported. Each sample was measured in triplicate except where otherwise indicated. When blood CA was measured, deionized water was substituted with blood and the measurement followed the same procedure. Bovine blood was purchased from Sigma-Aldrich and was stored in a refrigerator until the time of testing. At the conclusion of the measurement, the liquid droplet was cleaned from the sample surface with a paper towel.

The Ramé-Hart automated tilting base was used to measure ROA. The base was programmed to tilt 1 degree per second and frames were recorded 10 times per second. ROA was recorded for the first angle at which the droplet moved from its position. ROA were measured in triplicate and averaged, except where otherwise indicated.

Stretching Testing. Three custom stretching devices were made to analyze stretching properties of the hydrophobic materials. Each of the devices had two clamps to hold opposite ends of a stretchable material. The clamps were separated as a screw was turned. The first two stretching devices were designed with 3D modeling software and printed on a 3D printer. One of the devices was capable of stretching materials to 75% longer than their original length. The other device could stretch materials to 400% of their original length. The third stretching device was built on a micrometer controlled translating platform. Clamps were 3D printed and secured on the top of the platform. This device offered more precise control over the stretch length.

The stretching devices were placed on the stage of the goniometer used for the CA and ROA measurements. Samples stretched multiple times were placed in the appropriate 3D printed stretcher and elongated to 75% more than their original length. Then the screw was returned to its initial position. One stretch to 75% of its original length and returning to the initial position constituted a single stretch/relaxation cycle. Some samples were stretched and relaxed up to, or over, 100 times. The micrometer controlled stretching device was used when precise control over elongation was desired. Tests that confirmed a new wetting state observed in stretching superhydrophobic coatings used this stretching device.

Abrasion Testing. To evaluate the durability of the stretchable hydrophobic materials disclosed herein, a uniform abrasion test was conducted by applying 10 kPa pressure to sample coupons. The procedure described by Xuelin Tian et al. (Science 2016, Volume 352, Issue 6282, pages 142-143) was used to test durability. The sample coupons were sheets of solid latex approximately 7 by 7 centimeters and supported on their edges by a thin plastic frame. The samples were placed in a holder that lifted the center of the sample and held a round area (25 mm diameter) against a flat metal weight. The hydrophobic material to be tested was placed face down with the weight on top of it. The weight had a mass of approximately 250 grams and exerted a pressure of 10 kPa evenly across the round exposed area of the sample. The pressure applied was equivalent to submersion in water at a depth of 1 meter.

The weight was mechanically slid across a sheet of 1500 mesh SiC abrasive sandpaper. This sandpaper has SiC particles of approximately 4 microns, which serve as an abrasive surface. A string was attached to the weight and pulled by a rotating motor to ensure consistent sliding speed. The samples were pulled for about 30 cm at a speed of 3 cm per second. Samples slid across the sandpaper once were said to have been subjected to one abrasion cycle.

CA and ROA were measured before the first abrasion cycle and after each subsequent one. To simulate how samples were to perform with a shelf life, durability measurements were conducted on samples 24 hours, one week and one month after preparation. To determine the optimal dwell time between the application of liquid polymer and the application of particles samples were prepared with different dwell times and durability of each was tested with multiple abrasion cycles.

The stretchable hydrophobic materials disclosed herein retain their hydrophobicity after at least one abrasion cycle. In certain embodiments, at least 75% of the original hydrophobicity is retained after at least one abrasion cycle. For example, at least 80% of the original hydrophobicity is retained, at least 90% of the original hydrophobicity is retained, or at least 95% of the original hydrophobicity of the sample has been retained after at least one abrasion cycle. In an embodiment, the stretchable hydrophobic materials retain their hydrophobicity after at least two abrasion cycles, or after at least three abrasion cycles.

In one embodiment, the stretchable hydrophobic materials retain their hydrophobicity after at least four abrasion cycles. In an embodiment, at least 75% of the original hydrophobicity is retained after at least four abrasion cycles. For example, at least 80% of the original hydrophobicity is retained, at least 90% of the original hydrophobicity is retained, or at least 95% of the original hydrophobicity of the sample has been retained after at least four abrasion cycles.

Surface Area. The surface area of the particles was measured via gas adsorption (BET theory) using an Autosorb-iQ analyzer (Quantachrome Instruments). Powder samples of each type of particle were placed in glass vials and degassed prior to measurement. The surface area was measured using procedures as outlined in the instrument's instruction manual.

Imaging. High resolution images of the stretchable hydrophobic materials were obtained by scanning electron microscopy (SEM) (JEOL 6610-LV) in low vacuum mode at 10 kV to minimize damage to the materials. The samples were coated with a thin layer of conductive palladium prior to imaging. Unilaterally stretched samples were mounted on slides and held in a stretched position with polyimide tape and glue. To create a multi-laterally stretched sample, a portion of a latex glove was coated with a hydrophobic coating. Two points were marked on the surface and the distance between them was measured. The glove was then inflated like a balloon, stretching the latex evenly in all directions. The glove was inflated until the markings were a distance apart equal to about 225% of their original separation distance. A ½ inch metal washer with a ¼ inch hole in the middle of it was glued to the outside of the inflated glove. Glue held the latex visible at the center of the washer in a stretched position after the rest of the glove was deflated.

Transmission electron microscopy (TEM) was carried out using a JEOL 200CX microscope. Samples of the silica fibers were placed on a transparent TEM grid prior to imaging. Atomic force microscopy was performed on the stretchable hydrophobic materials in tapping mode driven at 317 kHz (Asylum MFP-3D-Bio) and profile data was used to show the micro- and nano-texture in the coating. 3D surface profiles were measured by optical profilometry (GT-I Contour Elite, Bruker Nano) in vertical scanning mode. As optical profilometry is a non-contact technique that is done in atmospheric conditions, samples were placed on the micrometer controlled stretching device and were carefully elongated in between images. Samples of superhydrophobic coatings were imaged by helium ion microscopy (Zeiss Orion Plus) with 25.0 kV acceleration and 1.0 µs dwell time. For each microscopy technique, a range of magnifications and working distances were used to collect images with a range of sizes for field of view.

Example 1

Liquid latex rubber (TAP Premium Liquid Latex Rubber) was diluted in a 1:1 ratio with water. The dilution was mixed well with a stirring rod. Diluted liquid latex was painted on a latex sheet substrate with a fine bristled paint brush. The brush was used to evenly spread the liquid latex into a uniform film. Fumed silica (Aerosil RX-50) with an HMDS shell was used, and one gram of fumed silica was mixed into 6 grams of hexane in a conical test tube and a lid was placed on the tube. The tube was shaken for 10 seconds and the test tube was then placed in an ultrasonic bath (Branson) for 15 minutes to allow for complete dispersion of the particles into the hexane.

The silica solution was removed from the ultrasonic bath and sprayed onto the film of liquid latex. Spraying of the fumed silica solution occurred immediately (within seconds) of the application of the liquid latex, using an IWATA Eclipse HP-CS airbrush connected to an IWATA Studio Series Silver Jet Single Piston Air Compressor operating at 30 psi. The propellant was compressed air. The tip of the airbrush was held approximately 30 cm from the liquid latex and moved in a smooth back and forth motion as the spray was applied. The airbrush was held at a distance such that much or all of the solvent in the silica/hexane solution evaporated prior to reaching the liquid latex. As such, the airbrush created a stream of fumed silica projected in the direction of the liquid latex. Spraying was ceased when the liquid latex sample took on a lighter color caused by the addition of silica particles, which was approximately 2-4 seconds for a 5 cm by 5 cm sample. The samples were then left to dry for at least 24 hours prior to testing, except where otherwise indicated.

This general procedure was used to apply the hydrophobic coatings to disposable latex and nitrile gloves. Opposing sides of the gloves were coated by spraying the particles from multiple angles and by rotating the gloves during spraying. Gloves were partially inflated to give the gloves the form of a hand. Inflated gloves were tested for hydrophobicity by holding them under a stream of water from a faucet and by measuring wettability.

Table 1 lists the characteristics of a series of hydrophobic materials prepared following the procedure of Example 1.

TABLE 1

Characteristics of unmodified and hydrophobic materials.

| Material | $H_2O$ CA (°) | $H_2O$ ROA (°) | Blood CA (°) | Blood ROA (°) |
|---|---|---|---|---|
| uncoated materials | | | | |
| Latex | 105 | >90 | 95 | >90 |
| Nitrile | 57 | >90 | 46 | >90 |
| Tyvek Tychem | 90 | 75 | 90.8 | >90 |
| Lotus leaf | 155 | 9.0 | | |
| Teflon | 89 | 15 | 99 | >90 |
| materials with hydrophobic coatings | | | | |
| Latex Lotus imprint | 110 | >90 | 58 | >90 |
| HP Latex | 156 | 12.9 | 151 | 10.9 |
| HP Latex stretched (175%) | 163 | 7.1 | 155 | 16.9 |
| HP Latex stretched (300%) | 158 | 18.6 | 156 | 22 |
| HP Latex after 100 stretches | 155 | 8.6 | 148 | 8.0 |

As seen in Table 1, the CA for natural rubber latex is normally 105 degrees, indicating that it is moderately hydrophobic. However, water droplets adhere to latex gloves and do not roll off or slide, even when the material is tilted to 90 degrees. In contrast, the nitrile gloves coated with the stretchable hydrophobic material made with liquid latex, as described in Example 1 (labelled as "HP Latex") had a CA of 156, indicating that the coating was superhydrophobic. In addition, the material also exhibited a low ROA of 12.9 degrees. With a biological fluid, bovine blood, the CA remained high at 151 degrees. Water and blood were both shed from the surface leaving a pristine dry material.

Table 1 also shows the wetting characteristics of natural rubber latex that was imprinted with the texture of a lotus leaf (labelled "Latex Lotus imprint"). This sample was prepared by first making a high fidelity negative mold of a natural lotus leaf using PDMS. The PDMS copied the micro and nano texture of the lotus leaf (in negative). The mold was separated from the leaf, cleaned with deionized water, and thoroughly dried. The negative mold was also cleaned with a UV ozone plasma cleaner. It was then coated with a molecular monolayer of trimethylchlorosilane to ensure clean separation from the latex poured over it. Liquid latex was poured over the mold and formed a thick (1-3 mm) layer as it dried. After complete drying, the latex was separated from the mold and texture of the lotus leaf was verified with a microscope. The table shows that the imprinted latex had a contact angle of 110 degrees and water droplets did not roll off the surface when tilted to 90 degrees. This result indicates that texture may not necessarily impart superhydrophobicity to the natural rubber latex.

Figure 8:
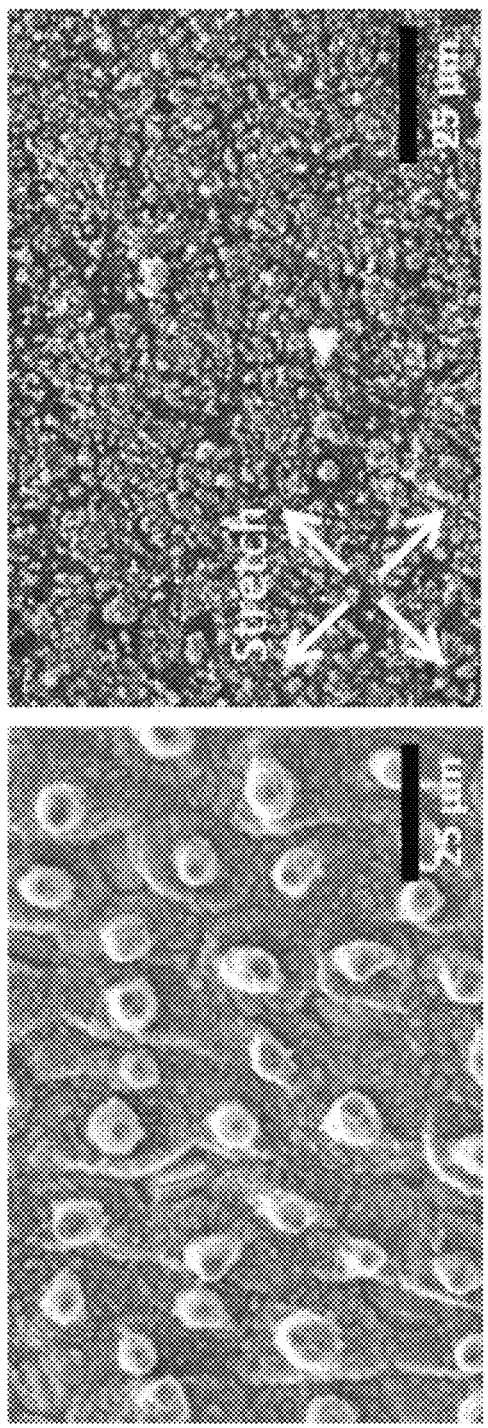
FIG. 8 shows scanning electron microscopy (SEM) images of a natural lotus leaf (left image) and of an exemplary stretchable hydrophobic material stretched uniformly in all directions to 225% of its original size as measured by the increase in distance between two points (right image).

FIG. 8 shows two scanning electron microscopy (SEM) images. On the left image, the surface structure of a natural lotus leaf is shown, with a structure of protrusions having a size of about 10 µm, covered by a nanoscale texture. Thus, the structure of the lotus leaf is hierarchical, with microstructural pillars that are about 10 µm wide and separated by about 10-20 µm that are coated with a nanotexture. On the right image of FIG. 8, the surface structure of the hydrophobic glove of Example 1 is shown, stretched uniformly in all directions such that two points on the material became separated by 225% of their original separation. The image shows that stretching has caused the uniform layer of surface embedded particles to become separated into agglomerates that are 1-10 µm wide and separated by 1-10 µm. The agglomerates of particles have nanostructured features that are a result of the individual particles. Thus, the act of stretching the material caused it to be transformed from a material having nanostructured features to a material having microstructured and nanostructured features.

Figure 9:
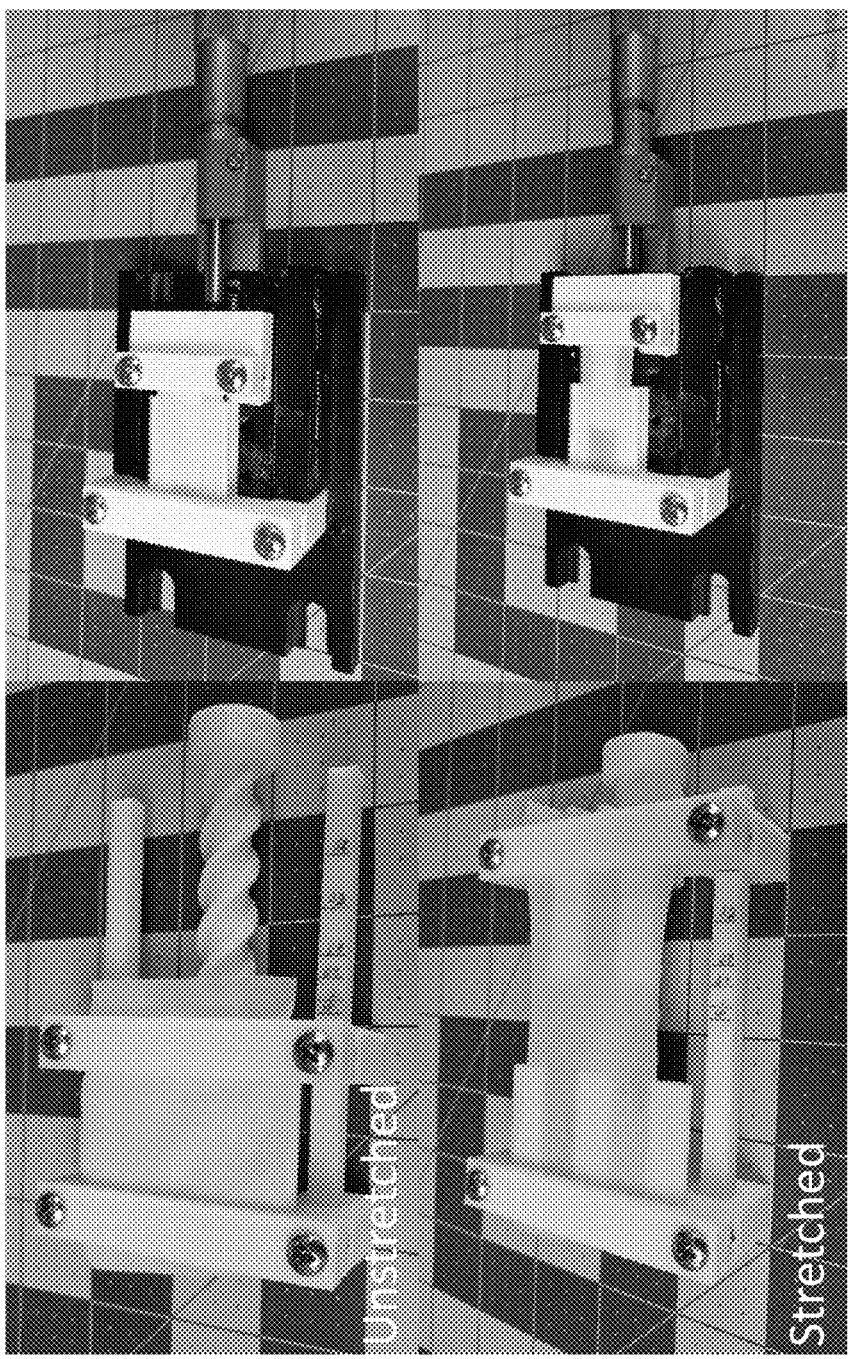
FIG. 9 is a series of photographs of stretching devices used to measure the wettability of embodiments of stretchable hydrophobic materials while being stretched in a controlled manner. The upper photographs show unstretched materials, and the lower photographs show stretched materials.

Since gloves are stretched and flexed during normal usage, the samples prepared above were placed into a stretching apparatus and the CA was measured as the material was stretched. FIG. 9 shows photographs of stretching devices used to measure wettability of stretchable hydrophobic materials while being stretched in a controlled manner. The upper photographs show unstretched materials, and the lower photographs show stretched materials. The photographs on the left side of FIG. 9 show the device capable of stretching materials to 75% longer than their original length, and the photographs on the right side of FIG. 9 show the device with a micrometer controlled translating platform.

Surprisingly, the CA increased as the hydrophobic material was elongated to 75% more than its original length. Table 1 shows that stretching the material once increased the CA to 163 degrees (labelled "HP Latex stretched 175%"). In a separate test, a sample of the hydrophobic material of Example 1 was stretched once to 300% of its original length (labelled "HP Latex stretched 300%") and this resulted in an increase in CA over the original. This data is shown in FIG. 10.

Figure 10:
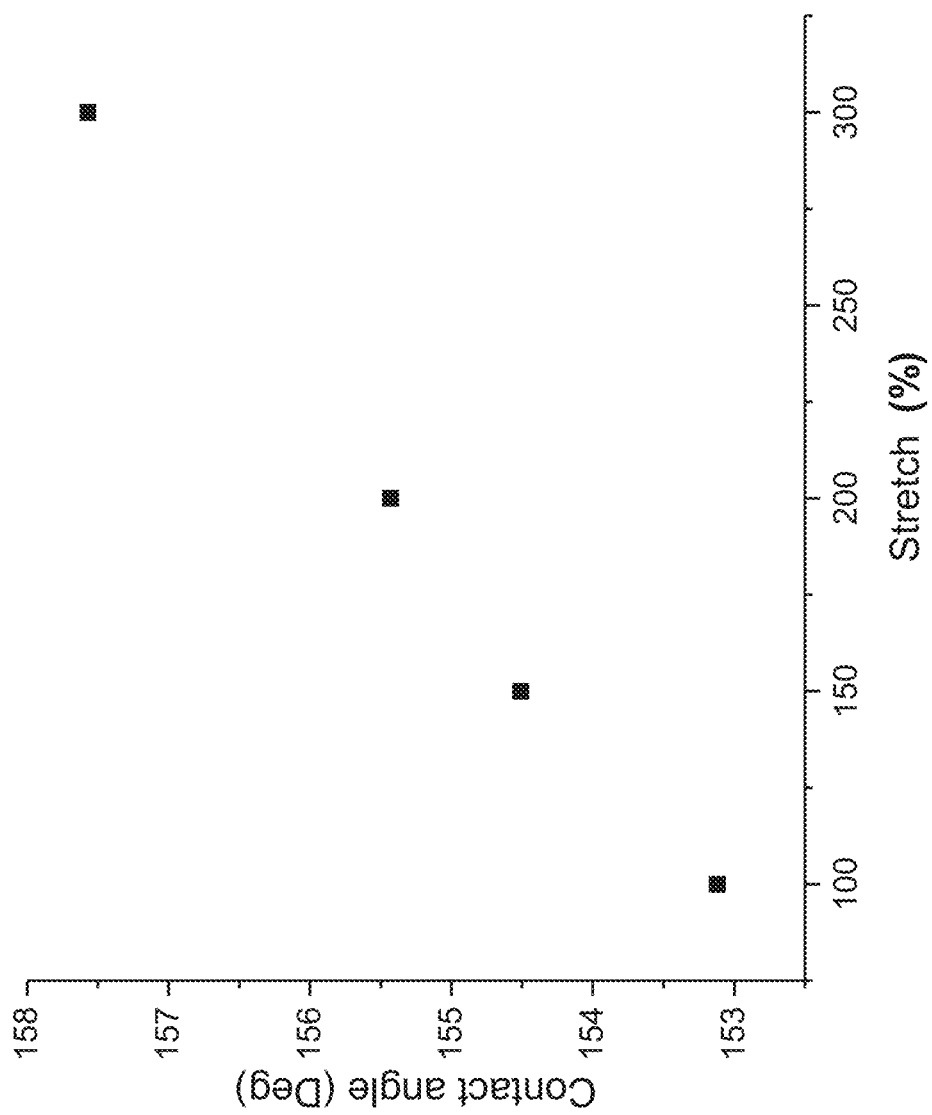
FIG. 10 is a graph of water contact angle (in degrees) versus the stretch (percentage in addition to its original length) for a nitrile glove coated with an exemplary stretchable hydrophobic material that is stretched up to 300% of original length.

FIG. 10 is a graph showing that the water contact angle increases as the hydrophobic material is stretched up to 300% of original length. The increase in CA as the glove was stretched was an unexpected and surprising experimental result. It was initially thought that the increase in CA with stretching was an artifact of the measurement technique, because stretching makes the material smoother which would make it easier to observe high contact angles. However, subsequent microstructural analysis revealed the mechanism by which the material's performance improved when stressed with stretching.

Figure 11:
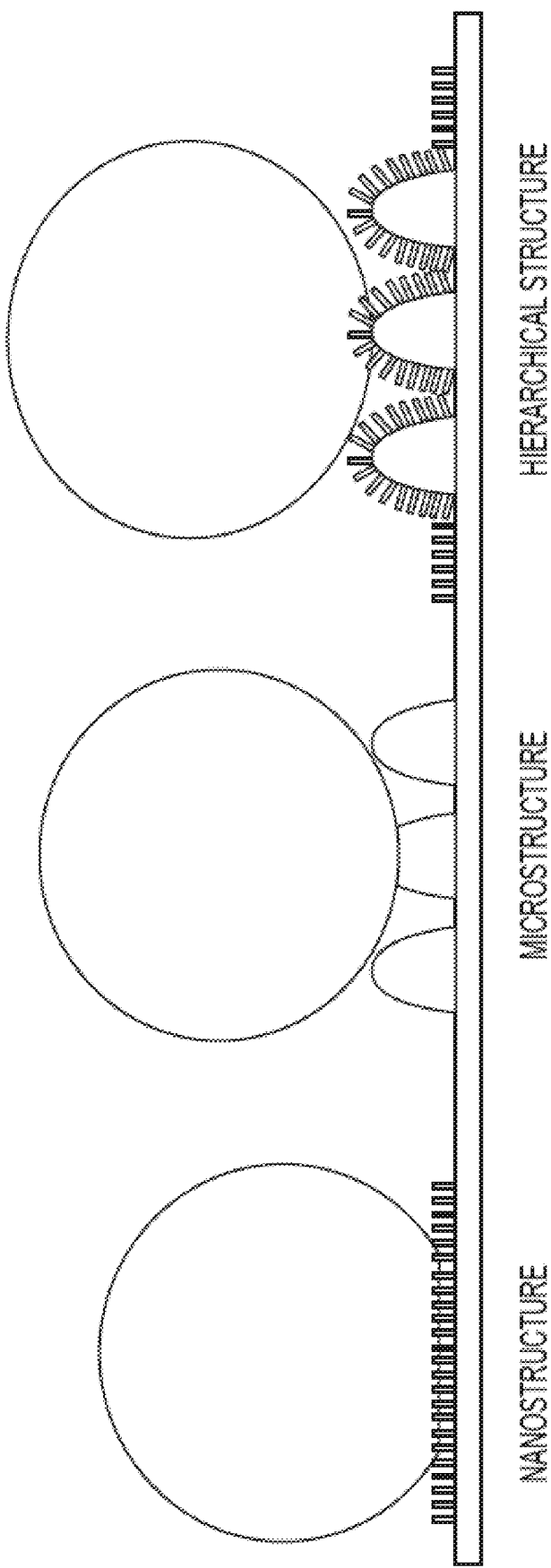
FIG. 11 is a schematic illustration comparing the micro- and nanostructure of water droplets on unitary and combination hydrophobic surfaces. A unitary conventional nanostructure is shown on the left side, a unitary microstructure is shown in the middle, and the hierarchical combination structure is shown on the right side.

This is shown schematically in FIG. 11. FIG. 11 shows a schematic illustration comparing the interaction of water droplets on unitary and combination hydrophobic surfaces. A droplet on a unitary conventional nanostructure is shown on the left side, a droplet on a unitary microstructure is shown in the middle, and a droplet on the hierarchical combination structure is shown on the right side. Certain of the hydrophobic materials described herein have a unitary nanostructure when they are not stretched, but upon stretching, they incorporate a microstructure in addition to the nanostructure. The images of FIG. 12 highlight this property.

FIG. 12 shows two SEM images, with the image on the left being the unstretched hydrophobic material and the image on the right being the stretched hydrophobic material of Example 1, with the direction of the linear stretch as indicated, stretched at 200% of its original length. The stretchable hydrophobic latex coating on the left shows a uniform nanotexture that results from the microlayer of embedded silica fibers. The surface texture seen in the image is limited to about the size of the fibers, which is 10 to 1000 nm (as seen in FIG. 7). The helium ion microscopy images of FIG. 7 show particles down to about 10 nm. The largest particles are 100-200 nm, but there appear to be chains and agglomerates that are longer, up to about 5 μm.

On the right side of FIG. 12, it can be seen that stretching has caused multiple cracks to open up in the layer of particles. The particles remain agglomerated into groups that are 1-50 microns in size. The cracks that formed are also 1-50 microns in size. Without being tied to a particular theory, it is believed by the inventors that the hydrophobicity of the material is, in part, due to the surface microstructure dimensional changes that occur as the material is stretched. Agglomerates of surface embedded fibers break apart into microscale aggregates separated by gaps and cause the emergence of micron-scaled texture. Alternating aggregates with gaps form microstructure that compliments the nanostructure intrinsic to the fibers.

Samples of the hydrophobic material of Example 1 were stretched to 175% of original length, relaxed from a stretched position, and repeatedly stretched 100 times to the same length to test the ability of the material to retain hydrophobicity after multiple uses. The hydrophobic material survived 100 stretches (labelled "HP Latex after 100 stretches") while maintaining not only a high CA above 150, but also a low ROA under 10. The only indication of degradation of the material was minor inelastic elongation, which is typical of the underlying latex substrate.

Figure 13:
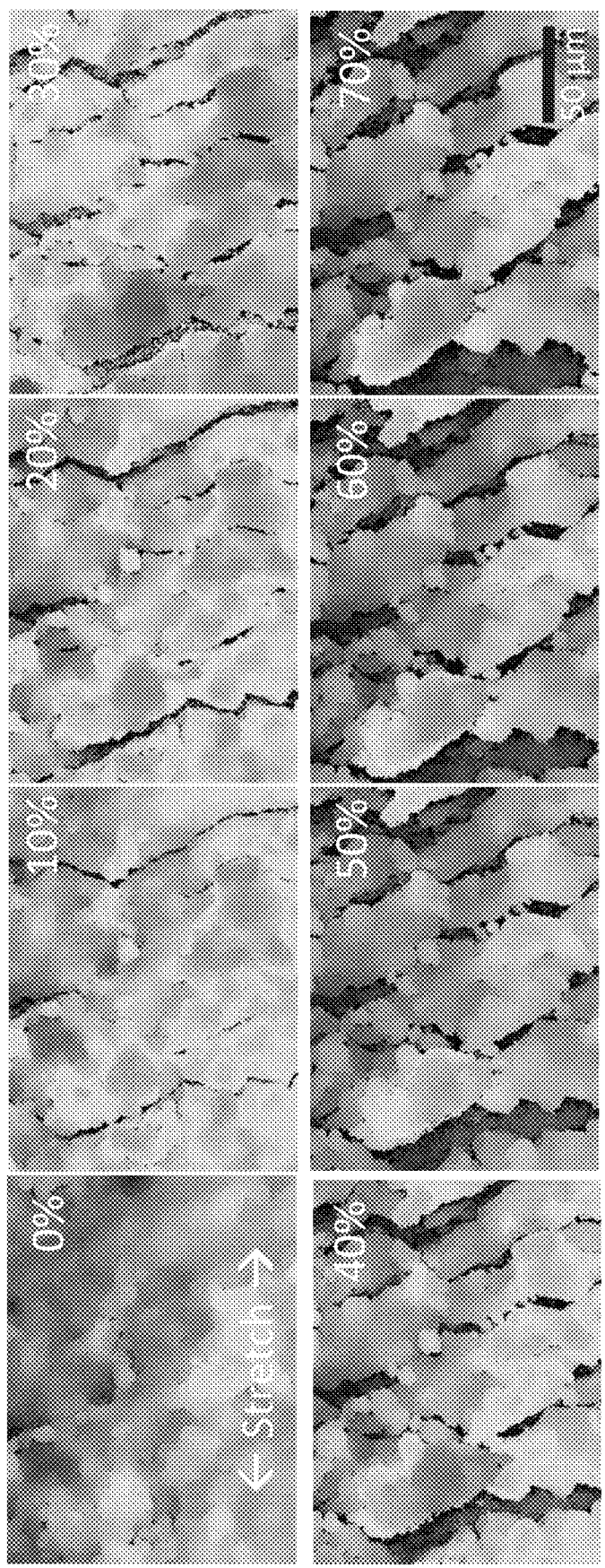
FIG. 13 shows a series of white light interferometric optical profiles of the surface of an embodiment of a stretchable hydrophobic material as it is being stretched from 0 to 70% of its original length. The percent stretch beyond the initial length of the material is indicated in the upper right of each image.

The stretchable hydrophobic materials described herein have the unitary nanostructure as shown in the left image of FIG. 11 when they are not stretched, but upon stretching, they incorporate a microstructure in addition to the nanostructure (as shown in FIG. 4). The images of FIG. 13 are white light interferometric optical profiles of the surface of the hydrophobic coating of Example 1 as it is being stretched. The percent stretch beyond the initial length is indicated in the upper right of each image. The images show the formation of dark cracks perpendicular to the stretch direction. In the images, the dark portions indicates a lower vertical position, thus the images show that cracks open up to reveal underlying latex and/or other particles. The cracks begin small (<1 μm) but eventually grow to more than 20 μm in some cases.

Both the lotus leaf and the hydrophobic materials described herein are hydrophobic in part due to their nanostructure, but the lotus leaf has an additional advantage due to its hierarchical structure. As illustrated in FIG. 4, however, some embodiments of the stretchable hydrophobic materials undergo a transition when stretched from a unitary to a hierarchical structure. FIG. 4 shows how the uniform layer of surface-attached silica fibers can spontaneously separate into microstructured islands. Separation of the islands further reduces wettability of the surface. Thus, in some embodiments, the stretchable hydrophobic materials not only maintain their hydrophobicity when stretched, but their hydrophobicity surprisingly improves. The stretched material may be more hydrophobic (having a greater contact angle) in part because it has a hierarchical surface structure.

Additional data from the samples of Table 1 are shown in FIGS. 14-19.

Figure 14:
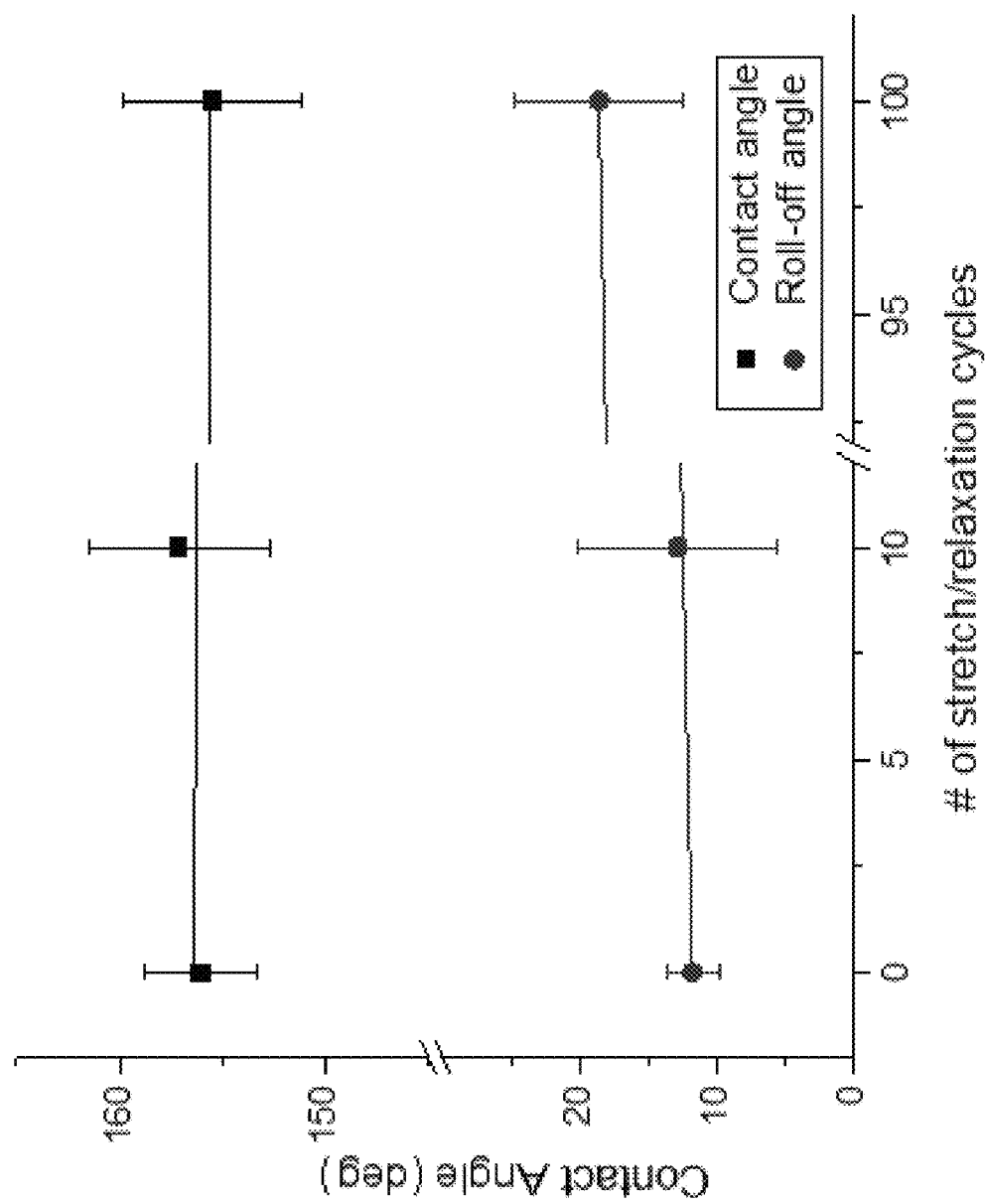
FIG. 14 is a graph of contact angle in degrees (squares) and roll-off angle (circles) versus the number of stretch/relaxation cycles for an exemplary stretchable hydrophobic material.

FIG. 14 is a graph of contact angle in degrees (squares) and roll-off angle (circles) versus the number of stretch/relaxation cycles for the stretchable hydrophobic material of Example 1, showing that the material retained its hydrophobicity when stretched up to 100 cycles.

Figure 15:
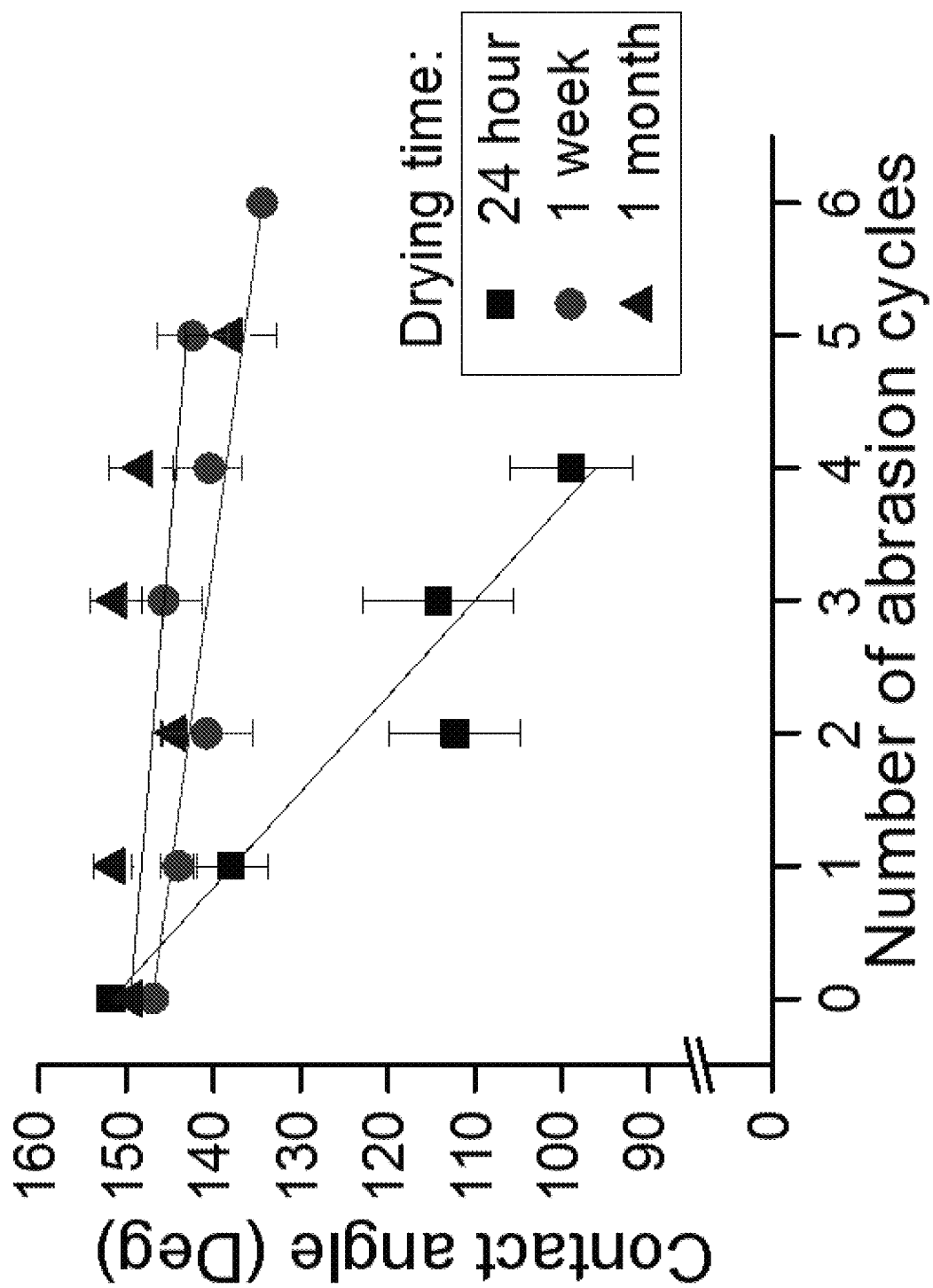
FIG. 15 is a graph of the water contact angle (in degrees) versus number of abrasion cycles for an exemplary stretchable hydrophobic material that has been dried for 24 hours (squares), one week (circles) and one month (triangles).

FIG. 15 is a graph of the water contact angle (in degrees) versus number of abrasion cycles for samples of the stretchable hydrophobic material prepared as described in Example 1, that have been dried for 24 hours (squares), one week (circles) and one month (triangles). The contact angle declines with more abrasion cycles, and samples left for at least 1 week were more durable. The solid lines show linear trends. The error bars show standard deviation (N=4).

As shown in FIG. 15, the initial CA was about 150 degrees for all samples regardless of the shelf life. Samples that were allowed to dry for one week and one month were more durable than samples dried for only 24 hours. After four abrasion cycles, some of the samples ripped because the underlying glove could not withstand the heavy abrasion. All samples ripped after 6 abrasion cycles. The samples with a hydrophobic coating dried for at least one week remained hydrophobic after six cycles of abrasion, with a CA of at least 135 degrees. The data demonstrate that drying the material for a period of time (such as at least one week) can improve the abrasion resistance of the material. Performance of the material did not decline with additional time between coating and testing. Hydrophobic coatings with abrasion resistance may have varied applications in which the coating may come into contact with other objects and may be abraded.

Figure 16:
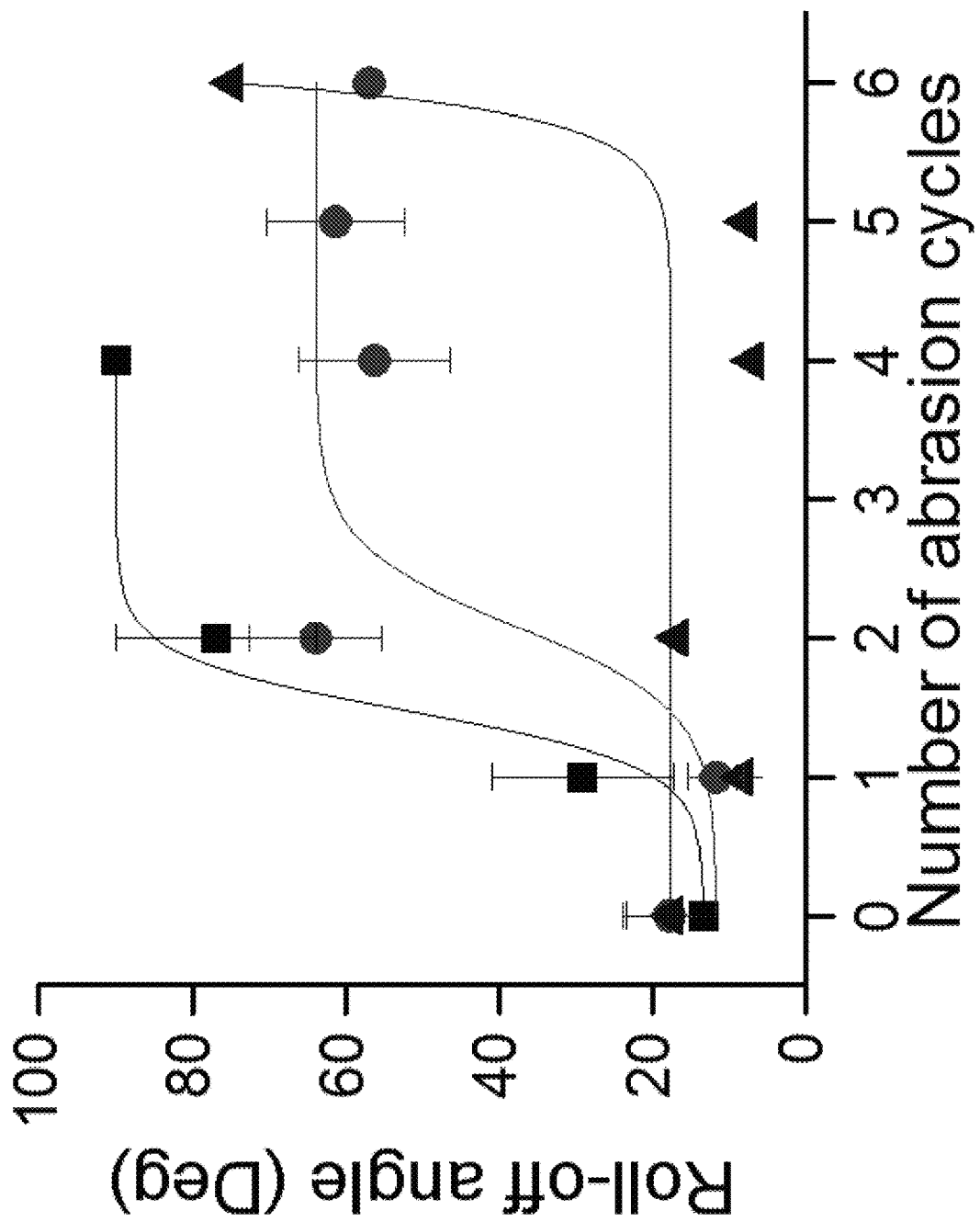
FIG. 16 is a graph of the roll-off angle (in degrees) versus number of abrasion cycles for an exemplary stretchable hydrophobic material that has been dried for 24 hours (squares), one week (circles) and one month (triangles).

FIG. 16 shows the effect of abrasion on the roll-off angle on samples of hydrophobic latex dried for 24 hours (squares), one week (circles) and one month (triangles). The solid lines shows sigmoidal Boltzmann fit curves. Error bars show standard deviation (N=4).

As shown, the roll-off angle increases with more abrasion cycles. Samples left for 1 month were very durable, maintaining a low ROA for 5 abrasion cycles. Durability of the hydrophobic latex may increase as the material has more time to fully dry and the silica fibers become fully embedded. The resistance to abrasion was very strong after 1 month as evidenced by the low roll-off angle, under 10 degrees, after 5 abrasion cycles. Increasing the time between application of the coating and testing may result in stronger attachment and embedding of the particle fibers, likely due to solidification of the latex polymer.

Figure 17:
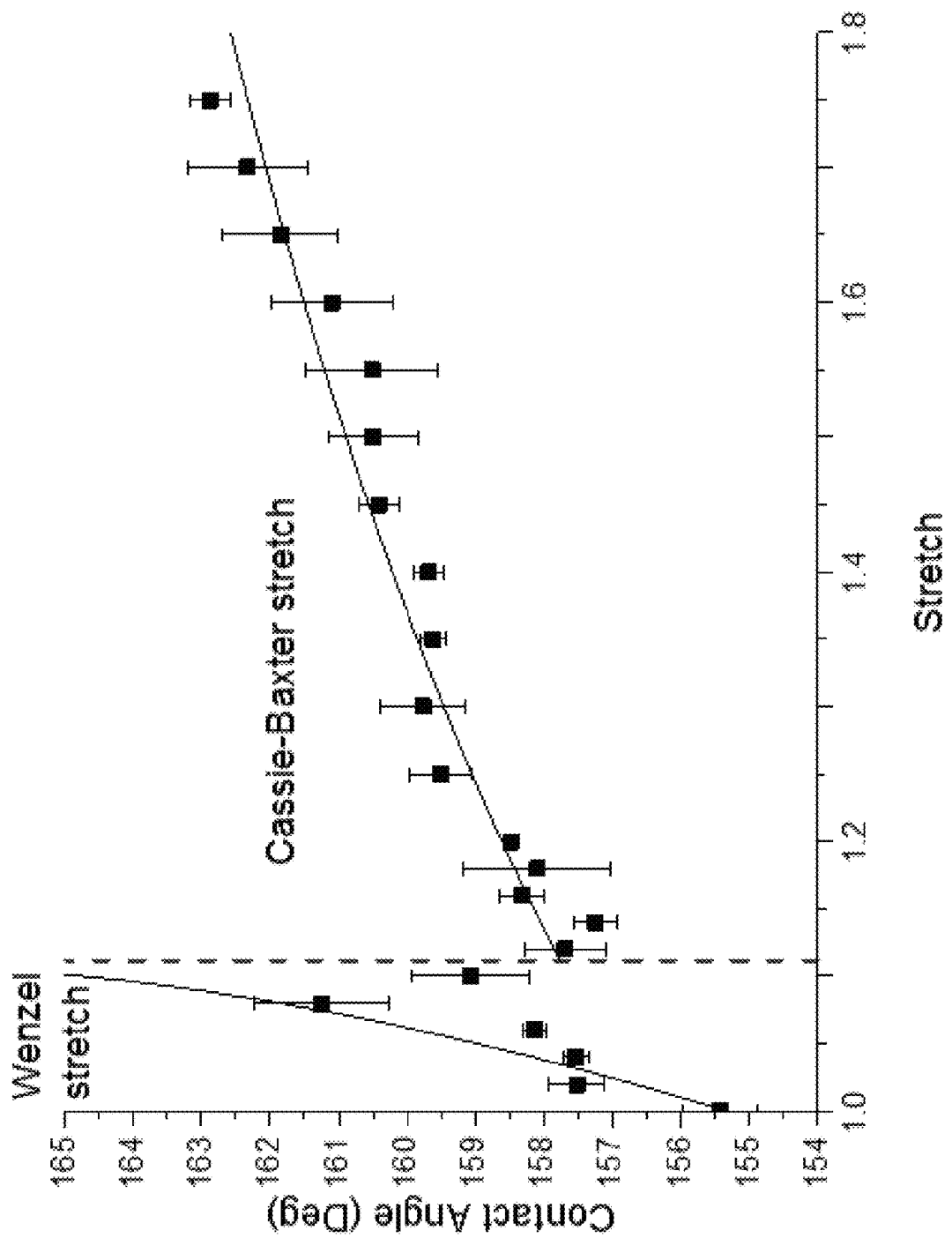
FIG. 17 is a graph of water contact angle (in degrees) versus the stretch (as a multiple of its original length) for an embodiment of an exemplary stretchable hydrophobic material.

FIG. 17 is a graph of water contact angle (in degrees) versus the stretch (as a multiple of its original length) for a sample of the stretchable hydrophobic material of Example 1, stretched up to 1.75 times its original length, showing the increased CA as the material is stretched.

Some embodiments of the stretchable hydrophobic material prepared as described in Example 1 may be superhydrophobic in addition to resisting abrasion. The combination of these attributes may lead to other advantageous effects. For example, embodiments of these stretchable hydrophobic materials may exhibit increased coating lifetime (the amount of time until the coating exhibits a significant observable decline in performance of a key attribute) and increased coating durability (ability to resist a single abrasion or impact of high magnitude, pressure, roughness, or friction). In addition, certain embodiments of these stretchable hydrophobic materials may improve grip or adhesion on a surface that would otherwise be rendered slippery when wet. A handle, bar, grip, or other object where grip is desired in a wet or periodically wet environment may be coated with a stretchable hydrophobic material as described herein and exhibit improved grip or adhesion. For example, a grip may be made from flexible or soft rubber and may be coated with stretchable hydrophobic material, which would repel water (which would act as an undesired lubricant) on its surface.

Figure 18:
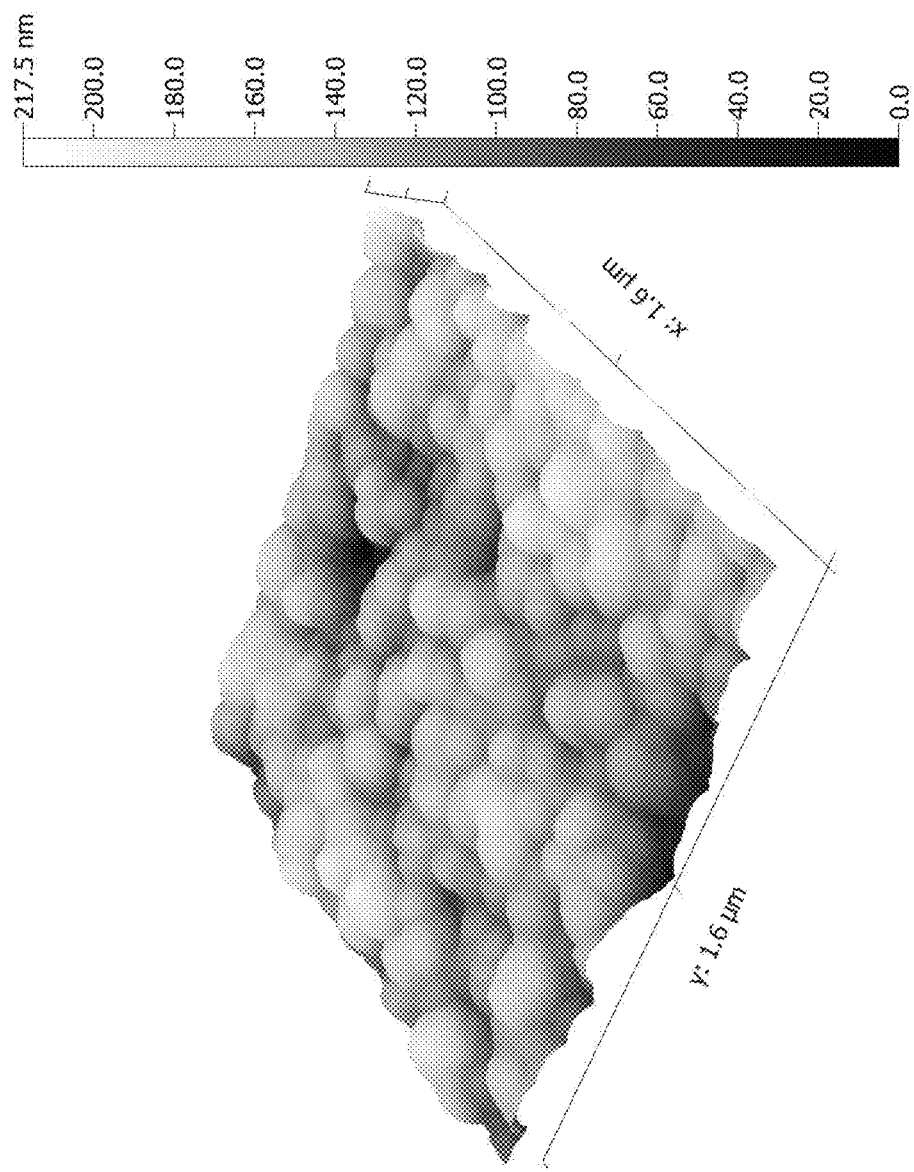
FIG. 18 is an atomic force microscope image of the surface of an embodiment of a stretchable hydrophobic material.
Figure 19:
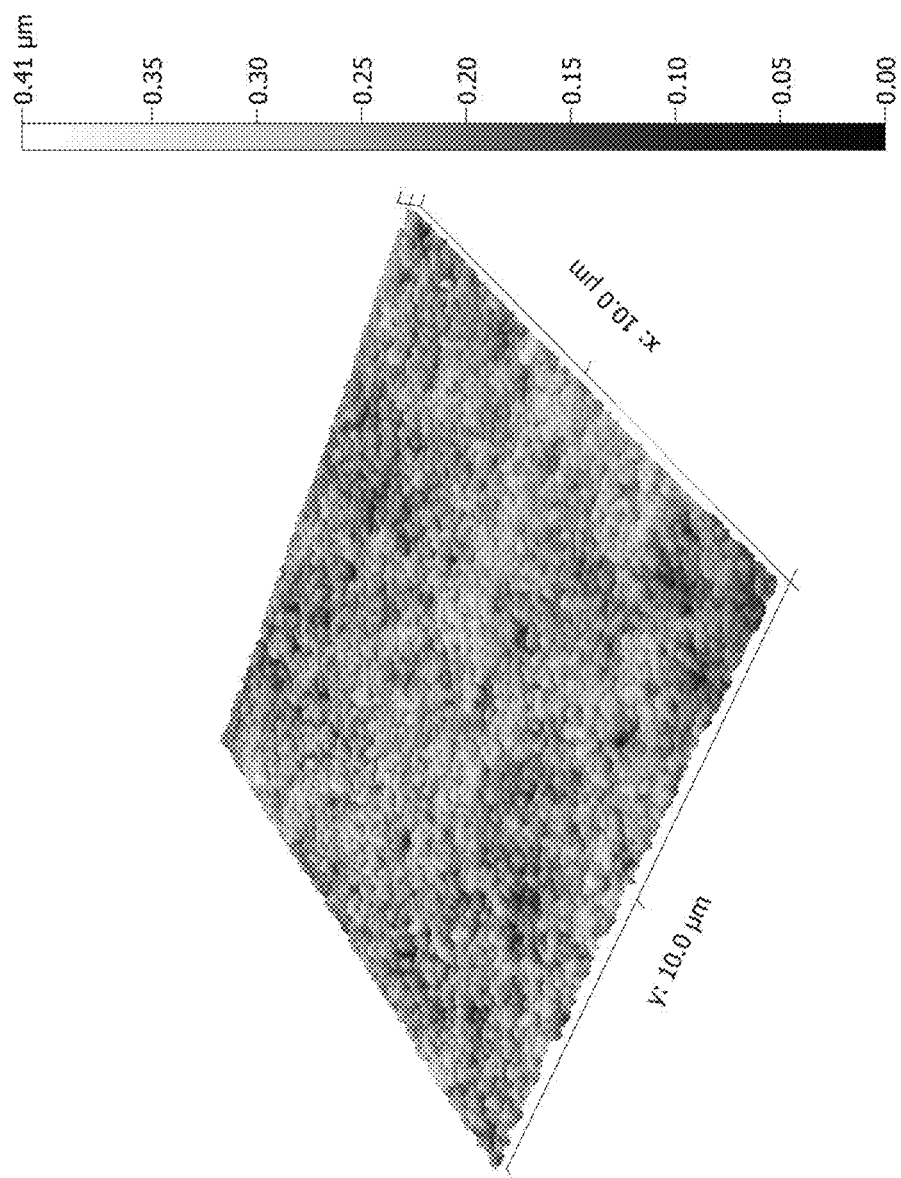
FIG. 19 is an additional atomic force microscope image of the surface of the stretchable hydrophobic material shown in FIG. 18, at a lower magnification.

The surface roughness of a sample of the stretchable hydrophobic material prepared as described in Example 1 is shown in FIG. 18 and FIG. 19. FIG. 18 is an atomic force microscope image of the surface of a 1.6×1.6 micron square of the sample, indicating that the surface is rough.

FIG. 19 is an additional atomic force microscope image of the surface of the same sample, at a lower magnification, of a 10×10 micron square of the sample.

Example 2

Generally following the procedure described in Example 1, a stretchable hydrophobic material was synthesized comprising liquid nitrile as the applied polymer. The liquid nitrile may be applied to a substrate by dip, spray, or brush coating. Prior to coating with liquid nitrile, a coagulant may be applied to the substrate, also by dip, spray, or brush coating. The coagulant may be aluminum sulfate, aluminum sulfate hydrate, calcium carbonate, calcium nitrate, calcium nitrate tetrahydrate, or another suitable coagulant, and may be diluted in a solvent prior to application on the substrate. The solvent may be water. The concentration of the diluted coagulant may be chosen to partially coagulate the liquid nitrile coated on the substrate surface. Partial coagulation of the liquid nitrile allows particles sprayed over the surface to become embedded. The process may also include heat treatment of the nitrile film, or simply allowing it to dry without additional heat.

A 0.25 M solution of calcium carbonate was prepared using 10.009 g of $CaCO_3$ (100.09 g/mol) in 100 mL of water. At least 25 mL of the solution was needed to submerse each 2 inch by 2 inch sample coupon in a plastic tray. Samples of both latex and nitrile substrate coupons were prepared. Each coupon was dipped upside down in the calcium carbonate solution for 30 seconds, pressing firmly on the back to ensure even wetting. The coupon was removed and allowed to dry for at least 2 minutes, at which time the substrate changed back to its original lighter color as it dried.

Once dry, the coupon was dipped in a solution of liquid nitrile polymer (Nychem 2000, Emerald Performance Materials) and rotated to each side to ensure even coating. The coupon was allowed to sit in the solution for approximately 30 seconds prior to spray coating. A solution of hexane/Aerosil RX-50 silica particles (8 g/1 g ratio) was prepared and placed into the airbrush cup. The coupon was removed from the liquid nitrile solution with tweezers and immediately sprayed with the particle solution following the spraying procedure described in Example 1.

Example 3

Generally following the procedure described in Example 1, a stretchable hydrophobic material was synthesized comprising liquid PDMS as the applied polymer. The PDMS may be applied to a substrate by dip, spray, or brush coating. Prior to coating the PDMS may be diluted in a solvent such as hexane.

A solution of PDMS (Down Corning Sylgard 182) was prepared by mixing the base and curing agent in a 10:1 ratio, vigorously with a stirring rod for 2 minutes. The PDMS was diluted in hexane in a 1:1 ratio. Samples of both latex and nitrile substrate coupons were prepared, and the PDMS solution was dip coated onto the desired substrate. The PDMS was allowed to partially cure (until tacky to the touch, but not solidified), about 30 minutes (thinner coatings can be less).

The samples were spray coated with a particle solution (hexane/Aerosil RX-50 solution in a 8/1 weight ratio) following the spraying procedure described above for the nitrile polymer. The samples may be left to dry at room temperature for 1 week or may be dried in a warming oven (up to 100° C.) for 30 minutes.

Each of the liquid polymers listed above (latex, nitrile, and PDMS) were applied to substrates using three different application methods: dip coating, spray coating, and brush coating. HMDS coated fumed silica was dispensed to the surface of each sample with an airbrush. The samples were dried for at least 24 hours. The following simple test was used to determine if the polymer coating method produced a coating that was hydrophobic with a low roll-off angle. A gentle stream of water was aimed at each surface using a transfer pipet. Approximately 1 mL of water was dispensed to the sample. If water formed droplets that rolled easily over or off of the surface then the sample was deemed hydrophobic. All coating methods used produced a hydrophobic coating.

Figure 20:
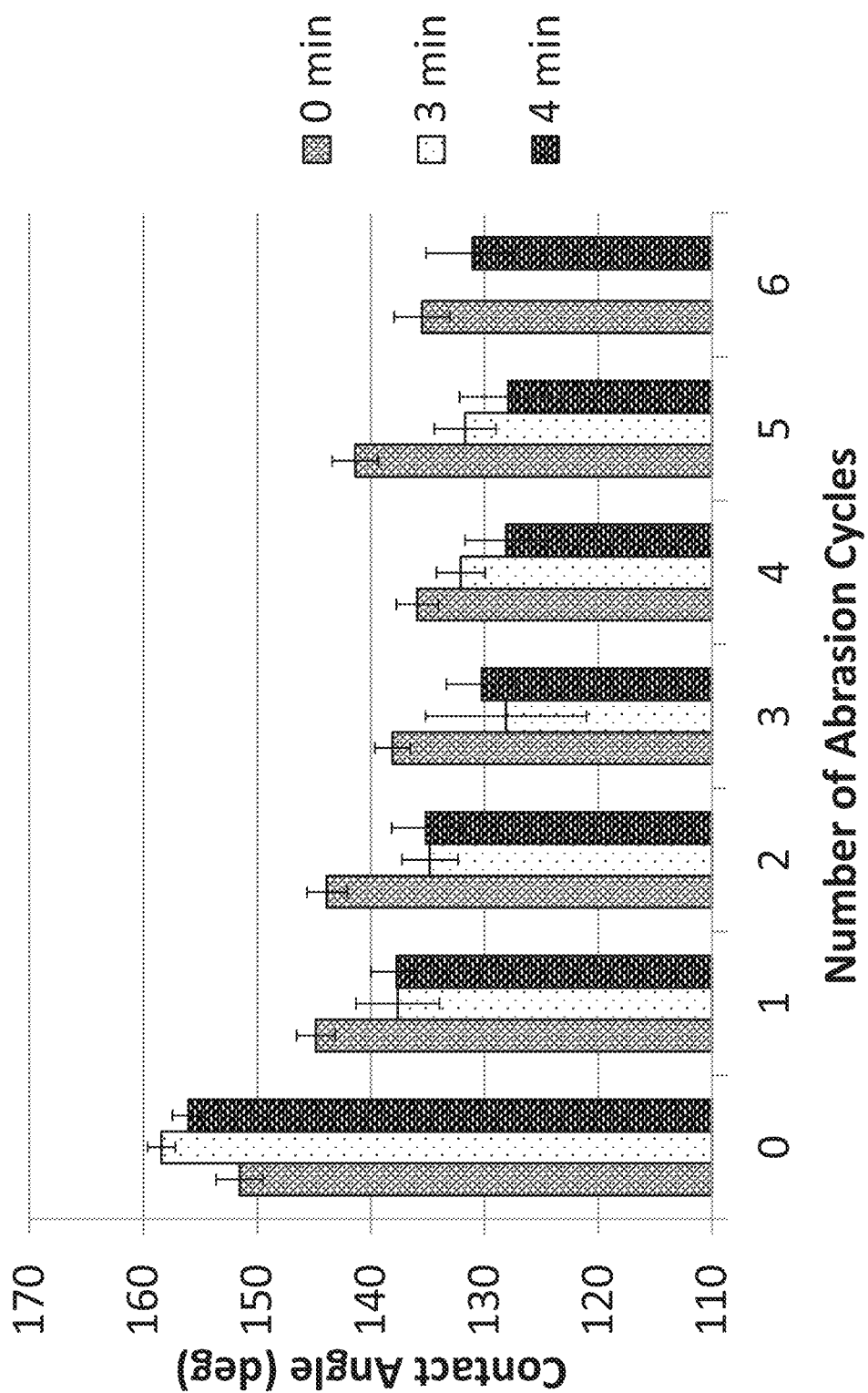
FIG. 20 is a graph of water contact angle (in degrees) versus the number of abrasion cycles for three different liquid polymer coating dwell times: 0 minutes (gray bar), 3 minutes (light bar), and 4 minutes (dark bar).
Figure 21:
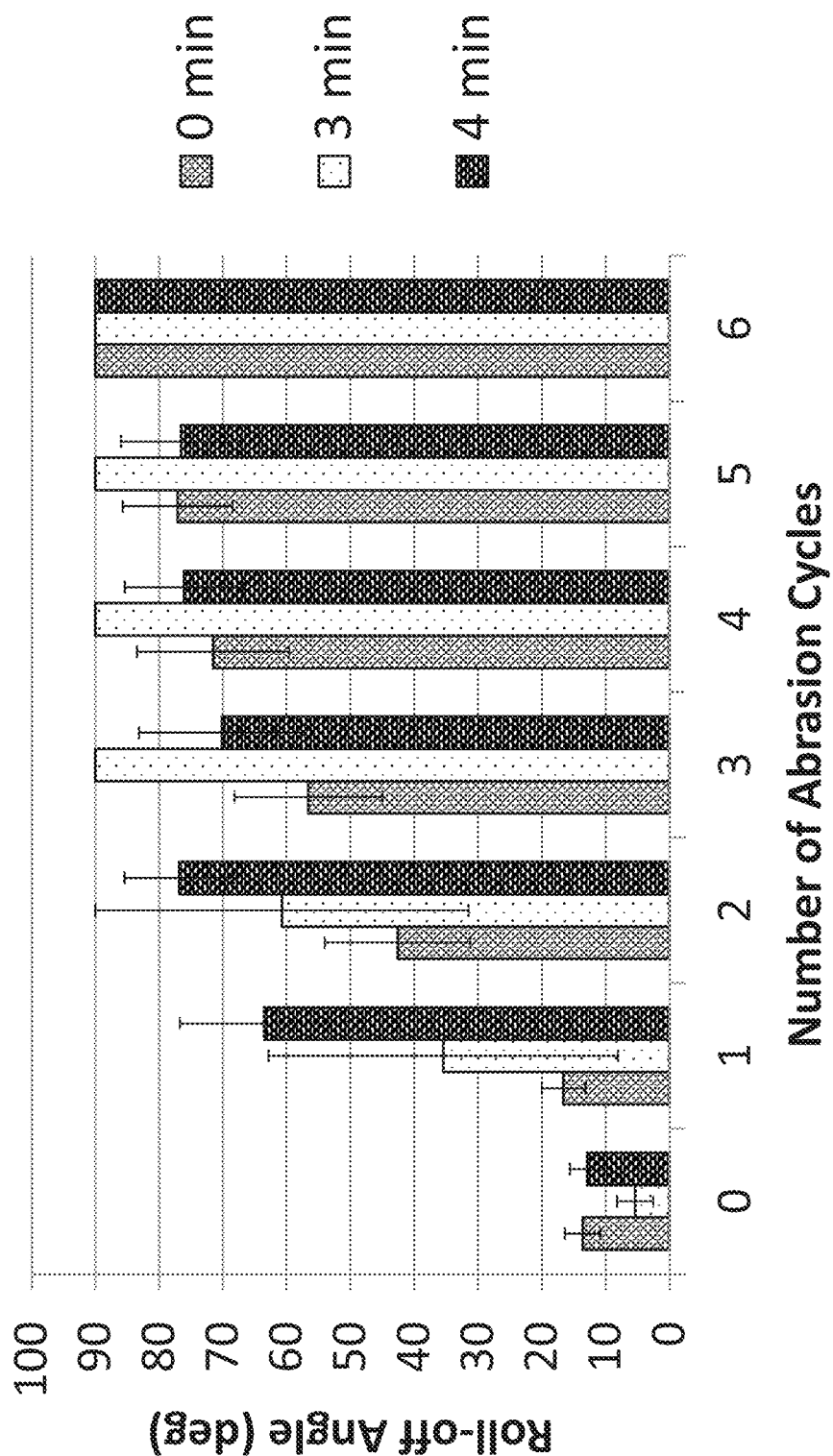
FIG. 21 is a graph of water roll-off angle (in degrees) versus the number of abrasion cycles for three different liquid polymer coating dwell times: 0 minutes (gray bar), 3 minutes (light bar), and 4 minutes (dark bar).
Figure 22:
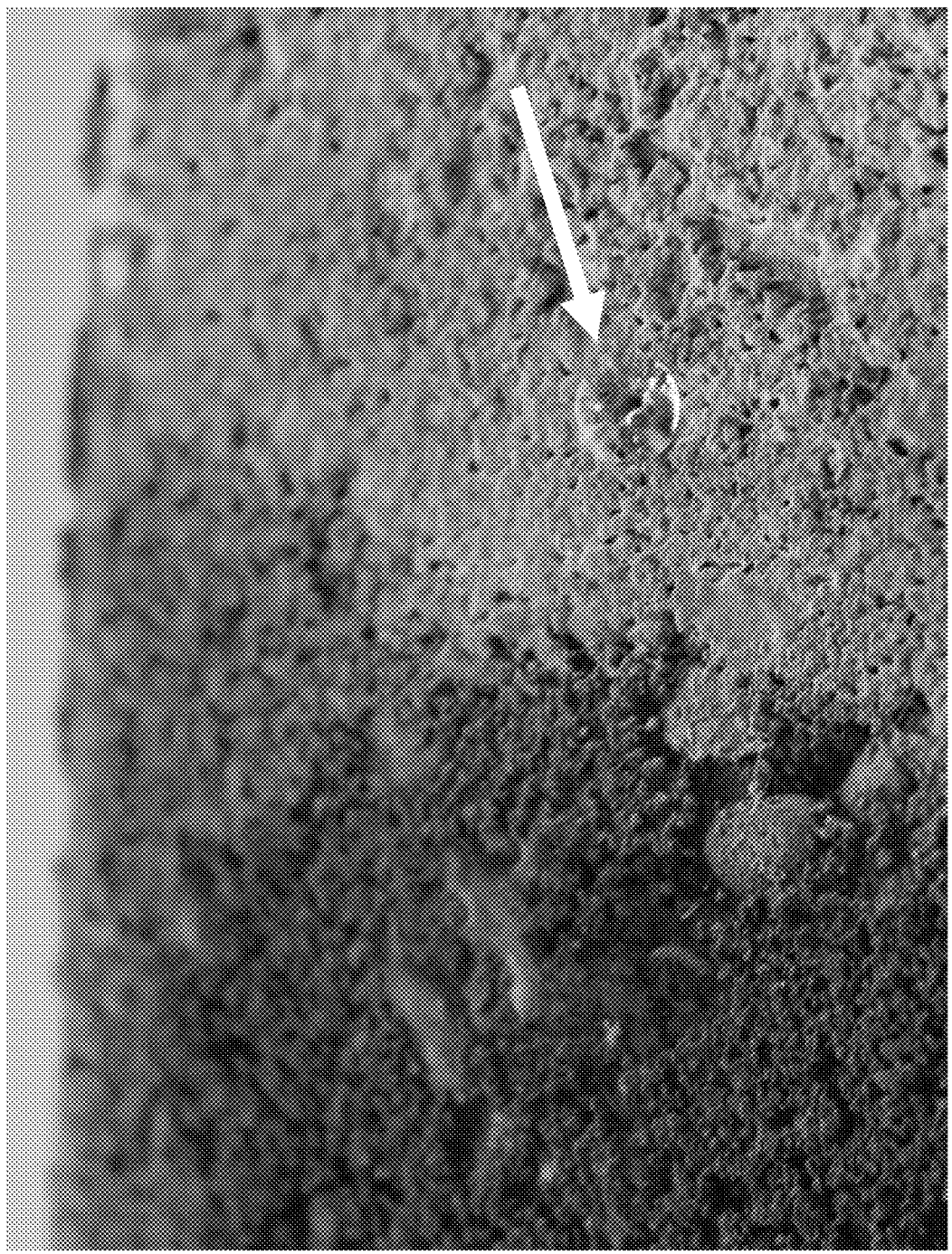
FIG. 22 is a photograph of a droplet of water on an embodiment of an exemplary stretchable hydrophobic coating applied to a concrete substrate. The uncoated left hand side of the concrete is wet with absorbed water.
Figure 23:
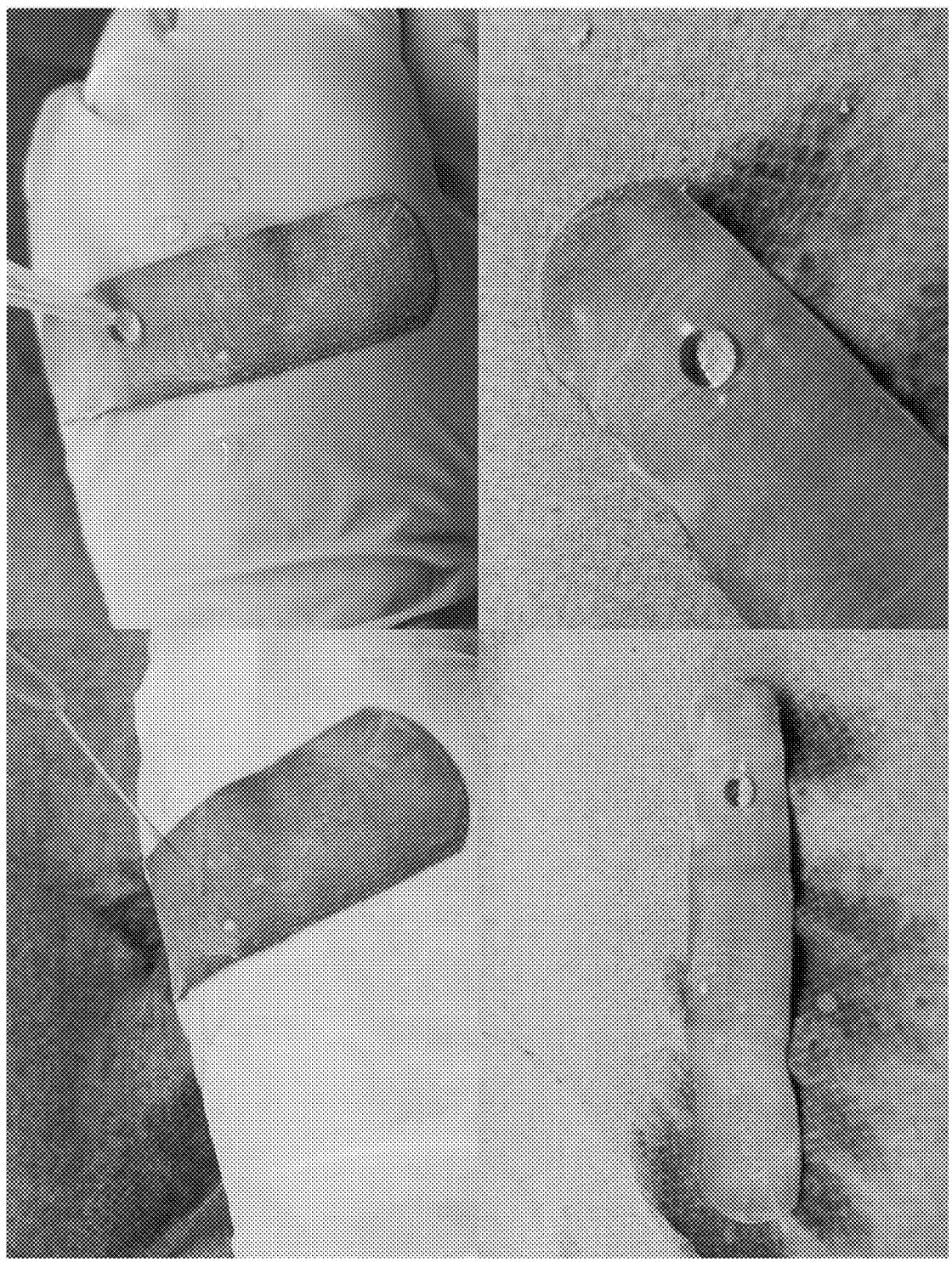
FIG. 23 shows a series of photographs of water droplets on a bandage coated with an exemplary embodiment of a stretchable hydrophobic coating.
Figure 24:
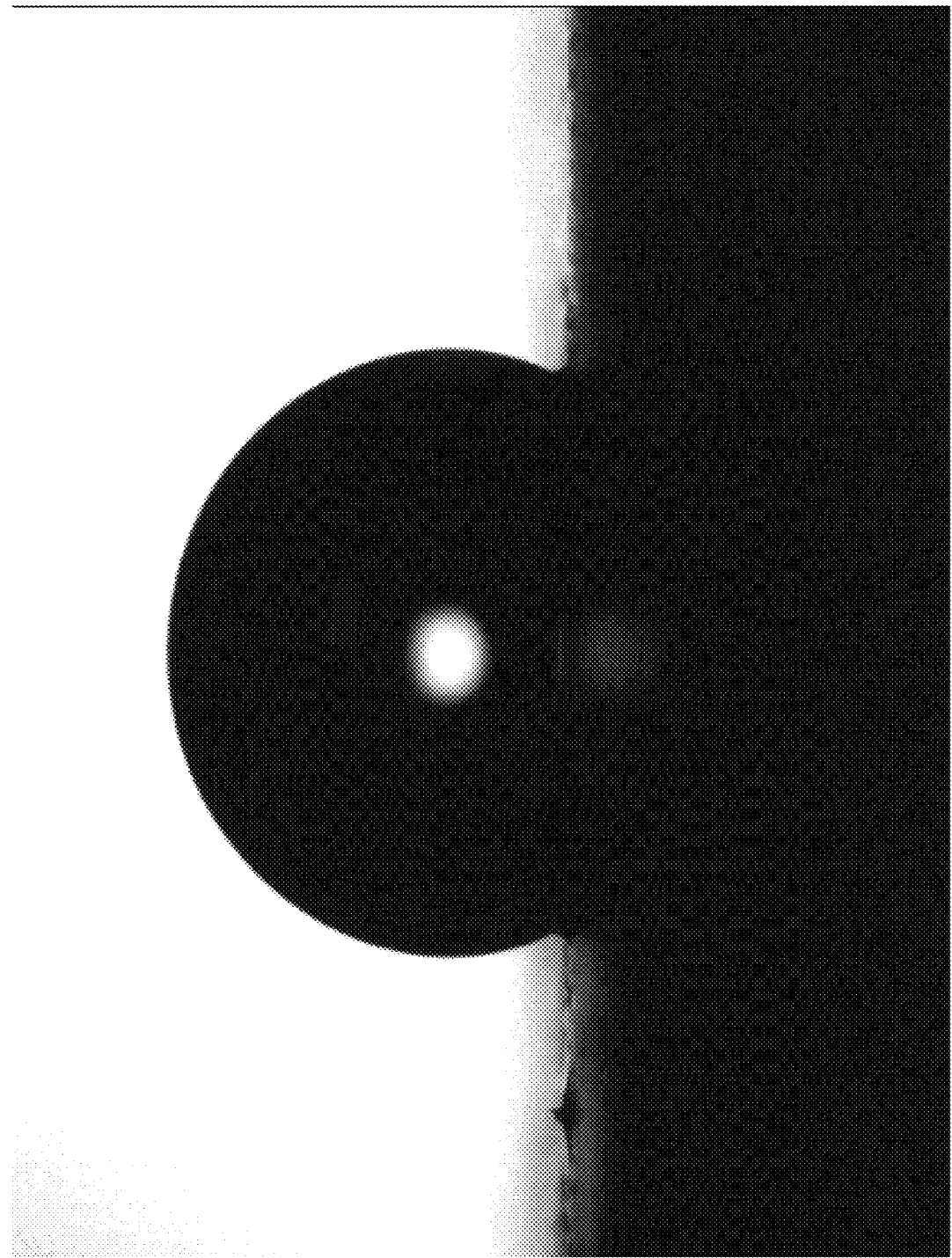
FIG. 24 shows the profile of a water droplet on an embodiment of an exemplary stretchable hydrophobic coating that is infused with a lubricant.

The dwell time between liquid polymer coating and dispensing particles onto the surface is relevant for embedding particles in the surface of the liquid polymer layer. The graphs shown in FIG. 20 and FIG. 21 show the effect of dwell time on abrasion resistance as measured by the change in contact angle and roll-off angle, respectively. Samples were prepared with liquid latex and HMDS coated fumed silica fibers on a solid latex sheet. The hydrophobic coatings were then subject to multiple abrasion cycles as described. Before the first abrasion cycle and after each one thereafter, the CA and ROA were measured. Three different liquid polymer coating dwell times are shown in the graphs: 0 minutes (gray bar), 3 minutes (light bar), and 4 minutes (dark bar).

The data show that spraying the particles immediately after coating the liquid polymer improved abrasion resistance. When a dwell time of 3 or 4 minutes was used the coatings suffered declines in contact angle after just one abrasion cycle. Likewise, coatings with long dwell times suffered an increase in roll-off angle after just one abrasion cycle. Coatings with short dwell times were more abrasion resistant and maintained a high CA and low ROA after 2, 3, or 4 abrasion cycles. One reason that longer dwell times may negatively impact the abrasion resistance of the coating may be that the liquid polymer begins to dry, solidify, or congeal at its surface, which may prevent embedding of particles partially or completely. When particles are merely dispersed over the surface of the underlying polymer without becoming embedded or partially embedded, they may be more susceptible to being removed from the surface under abrasion. Removing particles from the coating surface would likely have an adverse effect on its hydrophobicity.

Example 4

Particle composition, size, shape, and surface chemistry was evaluated. A selection of commercial particles were purchased and tested for their ability to make stretchable hydrophobic coatings, and the results are shown in Table 2. All particles were diluted in hexane in the ratio indicated in the table and sprayed onto a liquid latex film that was applied to a solid latex sheet substrate generally following the synthesis described in Example 1. Table 2 shows the material, surface chemistry, particle size range, morphology or shape, surface area, and CA.

TABLE 2

Particles used to make stretchable hydrophobic coatings.

| Material | Particle Core (shell) | Particle Size ($\mu m$) | Morphology | Surface Area ($m^2/g$) | CA (deg) | Particle:solvent mix ratio |
|---|---|---|---|---|---|---|
| AEROSIL OX-50* | Silica (N/A) | .04 | Fiber, globular chains of particles | 50 ± 15 | N/A | 1:19 |
| AEROSIL RX-50 | Silica (HMDS) | .04 | Fiber, globular chains of particles | 35 ± 10 | 159.4 | 1:6 |
| AEROSIL RX 200 | Silica (HMDS) | .012 | Fiber, globular chains of particles | 140 ± 25 | 160.4 | 1:15 |
| AEROSIL R 202 | Silica (PDMS) | .012 | Fiber, globular chains of particles | 100 ± 20 | 157.2 | 1:6 |
| AEROSIL R 208 | Silica (PDMS) | .012 | Fiber, globular chains of particles | 110 ± 10 | 153.0 | 1:9 |
| AEROSIL RX 300 | Silica (HMDS) | .007 | Fiber, globular chains of particles | 210 ± 20 | 159.4 | 1:12 |
| AEROSIL RY 300 | Silica (PDMS) | .007 | Fiber, globular chains of particles | 125 ± 15 | 156.2 | 1:12 |
| AEROSIL R 812 | Silica (HMDS) | .007 | Fiber, globular chains of particles | 260 ± 30 | 151.1 | 1:17 |
| AEROSIL R 812 S | Silica (HMDS) | .007 | Fiber, globular chains of particles | 220 ± 25 | 159.3 | 1:9 |
| PTFE Powder | PTFE (N/A) | 1 | Spherical | 21.5 | 135.0 | 1:6 |
| PTFE Powder | PTFE (N/A) | ≤12 | Spherical | 49.2 | 149.0 | 1:6 |
| PTFE Powder | PTFE (N/A) | 35 | Spherical | 20.7 | N/A | 1:6 |
| PTFE Powder | PTFE (N/A) | 200 | Spherical |  | N/A | 1:6 |
| Silica spheres | Silica (N/A) | 4 | Spherical | 13.6 | N/A | 1:6 |
| Silica spheres | Silica (N/A) | 8 | Spherical | 6.811 | N/A | 1:6 |
| Silica spheres | Silica (N/A) | 22-27 | Spherical | 193.5 | N/A | 1:6 |
| Silica spheres | Silica (N/A) | 45-53 | Spherical |  | N/A | 1:6 |
| Silica spheres | Silica (N/A) | 90-106 | Spherical |  | N/A | 1:6 |
| Silica spheres | Silica (HMDS) | 4 | Spherical | 64.9 | N/A | 1:6 |
| Silica spheres | Silica (HMDS) | 8 | Spherical | 55.3 | N/A | 1:6 |
| Silica spheres | Silica (HMDS) | 20 | Spherical | 84.0 | N/A | 1:6 |

*Same core as RX-50 particles

In Table 2, the CA indicates whether the coating was superhydrophobic (CA greater than about 150). The data shows that many particles with HMDS and PDMS surface chemistries were superhydrophobic. Samples with PTFE particles are known to be omniphobic and/or oleophobic. Aerosil OX-50 and Aerosil RX-50 are identical except that RX-50 has an HMDS coating and OX-50 is made of bulk silica with no surface shell coating. Unsurprisingly, the coating with silica surface chemistry was hydrophilic while the coating with HMDS surface chemistry was hydrophobic.

The data in Table 2 also shows that a variety of particle sizes from 7 nm to 12 $\mu m$ (as reported by the manufacturer) may be used to make hydrophobic coatings, as may particles with spherical, chainlike, and globular morphologies. Particles with surface area of about 1 $m^2/g$ up to about 300 $m^2/g$ may be used to make hydrophobic coatings. Generally, particles that did not result in hydrophobic coatings had hydrophilic surface chemistry (silica) or were not stable in solution and thus could not be dispensed by spraying to the surface of the wet latex film.

Example 5

Solvents used for particle deposition were also evaluated (spray, dip, paint, with and without solvents). Generally following the procedures for the synthesis of Example 1, a latex substrate was coated with a latex liquid polymer prior to spraying with HMDS-coated silica particles.

Hydrophobic particles may be applied or dispersed to the surface of a layer or liquid polymer by spraying the particles or solutions of the particles. The spraying may be done using compressed air or another propellant to dispense the particles in the direction of the liquid polymer such that when they come into contact with it they become embedded. The particles may also be applied to a liquid polymer layer by dipping the substrate comprising the liquid polymer in a solution of particles. A solution of hydrophobic particles may also be painted onto the liquid layer with the aid of a brush. Painting, dip coating, and spraying may use solutions containing particles or may use dry particles.

A variety of solvents evaluated for particle deposition are shown in Table 3. Of the solvents tested, only isopropyl alcohol was not suitable. Acetone and methanol both provided coatings with lower ROA and/or higher CA than the coatings made with hexane or pentane. Other solvents that suspend the chosen particle may also be used, such as using a fluorocarbon to suspend particles comprising a fluorinated surface. The solvent may also be used in conjunction with a stabilizing additive such as a co-solvent, surfactant, copolymer, soap, or other agent to aid in the suspension of particles.

TABLE 3

Solvents used to dilute hydrophobic particles prior to spraying on liquid latex.

| Solvent | CA (deg) | ROA (deg) |
|---|---|---|
| Hexane | 156 | 12.9 |
| Pentane | 156 | 8.2 |
| Methanol | 159 | 7.8 |
| Isopropyl Alcohol | 142 | 90 |
| Acetone | 156 | 5.1 |

Example 6

Substrates amenable to coating by a film of liquid polymer may be coated with hydrophobic coatings. Table 4 shows contact angles and roll-off angles for hydrophobic coatings applied to various substrates. Generally following the procedures for the synthesis of Example 1, the substrates were coated with a latex liquid polymer prior to spraying with HMDS-coated silica particles.

TABLE 4

Substrates that hydrophobic coatings were applied to and resulting CA and ROA.

| Substrate | CA (deg) | ROA (deg) |
|---|---|---|
| Teflon | 132.2 | 90.0 |
| Polypropylene sheet | 158.7 | 2.6 |
| Polyethylene tarp | 150.6 | 2.0 |
| Concrete | 137.1 | Not measured* |
| Wood (Smooth) | 150.1 | 3.5 |
| Cork | 146.8 | 23.2 |
| Tyvek Tychem | 153.5 | 8.1 |
| Latex sheet | 156.1 | 12.9 |
| Nitrile sheet | 158.4 | 11.3 |
| Glass slide | 161.2 | 5.4 |
| Fabric | 147.0 | 12.1 |
| Bandage | 154.1 | 14.3 |
| Stainless steel | 159.4 | 6.3 |

*Concrete could not be tilted; droplets were mobile on the surface.

With the exception of Teflon, all substrates tested had coatings with high droplet mobility (low ROA). Pure Teflon could not be coated evenly with water based liquid latex because it is hydrophobic. In some cases, materials that are rough or have irregular surfaces (fabric, concrete, bandage) had lower CA or higher ROA than expected, though this may result from a difficulty of measuring CA on rough surfaces with drop shape analysis and/or the tendency of water droplets to settle into small depressions in the surface.

FIG. 22 is a photograph of a droplet of water on a stretchable hydrophobic coating applied to concrete. The uncoated left hand side of the concrete is wet with absorbed water. Measurement difficulty with rough surfaces leads to an apparent contact angle below 150 and the depressions may result in a roll-off angle higher than expected. Nonetheless, the coating exhibits hydrophobic characteristics, namely high droplet mobility over the surface.

When applied to smooth substrates (glass, polypropylene, and polyethylene), the CA of the hydrophobic materials are generally high and the ROA are low. Articles or substrates that are not amenable to application of hydrophobic coatings may be made amenable by applying an intermediate coating or tie coat.

Example 7

A stretchable hydrophobic coating was applied to a bandage. A bandage may be a simple Band-Aid or another form of adhesive wound dressing. The stretchable hydrophobic coatings may render the bandage partially or completely waterproof, which may prevent infection of a wound.

A commercially available fabric bandage (Flexible Fabric, American White Cross) was removed from its sterile packaging. Liquid latex was applied over the bandage and a solution of HMDS-coated fumed silica was sprayed over the liquid latex, following the procedure as described in Example 1. The coated bandage was dried for 1 week and CA and ROA were measured (see Table 4). The coating was subjected to water droplets and a stream of water from a transfer pipet.

FIG. 23 shows a series of photographs of water streams or droplets being applied to the flexible bandage coated with the stretchable hydrophobic material. An advantage of this type of bandage is the ability to maintain, and perhaps improve, its hydrophobicity as the bandages is bent, flexed, and stretched due to movement of the wearer. Such movement would not diminish the hydrophobicity of coated bandages or other wound wraps or dressings.

Example 8

A stretchable hydrophobic material may be infused over its surface with a lubricant or oil. While this lubricant infused coating may not have a contact angle over 150, it may be considered superhydrophobic if it has a low roll-off angle. Samples of non-lubricated hydrophobic coatings were prepared according to the procedures of Example 1. Liquid latex was painted on a sheet of solid latex and a solution of HMDS coated fumed silica fibers (diluted 6:1 in hexane) was sprayed over it. The sample was dried for more than one week. A transfer pipet was then used to apply 0.5 mL of fluorocarbon oil (DuPont Krytox 103) over a sample area of approximately 2.5 square inches. The sample was left for about 15 minutes to allow the oil to infuse throughout the surface. CA and ROA were measured as described above. CA was also measured as the material was stretched to 68% of its original length. The CA of the lubricant infused material was 118.5±1.5 degrees and the ROA was 1.7±0.9 degrees, with the error representing standard deviation among 3 replicate samples.

FIG. 24 shows the profile view of a water droplet on the stretchable hydrophobic coating infused with a lubricant. Table 5 shows the CA as the lubricant infused coating was stretched.

TABLE 5

CA of a lubricant infused hydrophobic coating while being stretched.

| % stretch | CA |
|---|---|
| 0% | 113 |
| 5% | 115 |

TABLE 5-continued CA of a lubricant infused hydrophobic coating while being stretched.

| % stretch | CA |
|---|---|
| 11% | 122 |
| 16% | 117 |
| 22% | 119 |
| 27% | 117 |
| 34% | 121 |
| 41% | 120 |
| 55% | 117 |
| 68% | 119 |
| Return to 11%* | 113 |

*Sample relaxed to near original length

Measurements show that the CA is stable between 113 and 122 degrees. Droplets were mobile over the surface under all stretched conditions. The data also shows that the coating maintains a CA of 113 when relaxed from a stretched state to near the original length (11%).

Example 9

A stretchable hydrophobic material may be made using fluorinated silicone as the liquid polymer applied to a substrate, generally following the synthesis of Example 1. Hydrophobic particles will be sprayed over the liquid fluorinated silicone polymer as described prior to drying of the polymer. The fluorinated silicone may be a paint, an antifouling paint, or a foul-release coating. Fluorinated polymers are generally understood to be omniphobic and/or oleophobic.

Example 10

A stretchable hydrophobic material may be made with particles having a ceramic, polymeric, or metallic cores with a hydrophobic shell, generally following the synthesis of Example 1. The core of the particles may comprise titania, alumina, silicone, siloxane, latex, polystyrene, silver, copper, zinc oxide, or carbon. The shell of the particle may comprise any of the hydrophobic shell compositions described above.

Example 11

A stretchable hydrophobic material may be made with particles that are ovals, tubes, rod-like, chains, fibers, or combinations of these shapes, generally following the synthesis of Example 1.

Example 12

A stretchable hydrophobic material may be made with hydrophobic particles deposited on liquid polymers using alternative methods but generally following the synthesis of Example 1. The particles may be propelled towards the liquid polymer in a dry state and without a solvent. Compressed air, electrostatic potential, pressure, or gravity may be used to direct the particles toward the liquid polymer. The hydrophobic particles may form a raft or film on the surface of a liquid similar to a Langmuir-Blodgett film. The films may be formed on one liquid and transferred to another or the film may be formed on the surface of the desired liquid. The Langmuir-Blodgett process may be used to make ordered arrays of hydrophobic particles. These arrays may be transferred to the surface of a liquid polymer and dried thereon to create a stretchable hydrophobic coating.

Example 13

Mathematical Model. The data indicates that stretching water-impinged nanostructured coatings may induce a Wenzel/Cassie-Baxter hybrid superhydrophobic wetting state. Surface texture plays a role in the design of hydrophobic materials and coatings. Textured superhydrophobic materials have generally been designed on the basis of two models for hydrophobicity: the Wenzel model, in which roughness increases surface area; and the Cassie-Baxter model, in which air trapped in interstitial spaces prevents full surface wetting. Micro- and nano-structured materials designed to support the Cassie-Baxter state can suffer from limitations of durability inherent to the size of surface features. Some embodiments of the stretchable hydrophobic coatings are embedded in stretchable substrata that exhibit a hybrid Wenzel/Cassie-Baxter wetting state. In an embodiment, a nanostructured coating embedded in flexible natural rubber latex exhibits a sharp increase in contact angle with moderate stretching (<11%) followed by a steady increase in contact angle with further stretching (11-300%). An extension and combination of classic wetting models can explain this surprising result.

Textured surfaces can be vastly more hydrophobic than smooth surfaces, a result that cannot be achieved through surface chemistry alone. Superhydrophobic (SHP) materials are inspired by examples from nature including the leaf of the lotus flower, the back of the Namib Desert beetle, and the legs of the Gerridae water strider. These natural wonders depend on hierarchically textured wax crystalloids, asymmetric millimetric bumps, and fine nanogrooved hairs, respectively, to induce hydrophobicity. Unfortunately, these complex geometries are often as delicate as they are remarkable. Micro and nanoscale objects are inherently fragile and as such even carefully mimicked synthetic materials can lack physical durability.

The design of superhydrophobic materials with improved durability has focused on preventing the tendency of a wetting interface to transition from the Cassie-Baxter regime to the less desirable Wenzel state. Both states can lead to a high CA, but the Cassie-Baxter state is advantageous because it also exhibits high droplet mobility, as measured by low ROA and low contact angle hysteresis (CAH). In the Wenzel state, droplets fully impinge on the surface texture and are strongly pinned to the surface as a result. Recent attempts to make mechanically robust Cassie-Baxter regime materials have used unique multi-level geometries, modified surface chemistry, repairability, and self-healing. The transition from a Cassie-Baxter state to a Wenzel state can be reversed after a drying cycle, but not typically when the material is still wet.

Better understanding transitions in superhydrophobic wetting states during and after abrasion and other physical perturbations may lead to the better design of inherently robust superhydrophobic materials. It is known that the Cassie-Baxter state regresses to the Wenzel state when the interface is perturbed by pressure from liquid impingement or physical disruption of surface roughness. The transition can also be precipitated by biological growth. The use of superhydrophobic materials in healthcare and medicine or marine settings has been hindered by this limitation. Prior studies have demonstrated methods to make superhydrophobic materials that can bend, although proper control of surface morphology is the main challenge for many techniques especially when applied to flexible and stretchable materials such as gloves and textiles.

Embodiments of the stretchable hydrophobic materials disclosed herein extend the traditional models of wetting to explain the surprisingly robust hydrophobicity of nanotextured materials that are capable of stretching. A previously unobserved hybrid Wenzel/Cassie-Baxter state of wetting can explain the sharp increase in contact angle of moderately stretched superhydrophobic materials.

To examine the wetting behavior of stretching superhydrophobic surfaces, a composite coating of hydrophobic fumed silica fibers embedded into the surface of a thin layer of natural rubber latex was created as described in Example 1. The fibers were coated with HMDS to lower their surface energy. The coating was applied to latex sheets that could stretch, bend, and flex during study of surface wetting. Silica was applied in a uniform layer over the underlying latex (see FIG. 5). The surface texture is nanoscale and lacks the microscale bumps characteristic of lotus-type superhydrophobic surfaces. Nonetheless, the coating exhibits Cassie-Baxter state wetting with high CA (156°) and low ROA (12.9°).

The unstretched surface is shown in the scanning electron micrograph in the left side of FIG. 12. As the material is stretched linearly, or in multiple directions (see FIG. 8), the surface layer of silica breaks apart into microscale agglomerates. As this transition occurs, the material more closely resembles the structure of the lotus leaf because the uniform nanotexture is separated by microscale gaps. The process is reversible after multiple stretch/relaxation cycles. After the first stretch, the surface never regains perfectly homogeneous surface nanotexture. Rather, it has a familiar mixture of nano and microtexture.

In these SEM images, the uniform, densely packed layer of hydrophobic fumed silica fibers embedded in a latex coating prior to stretching is shown. The material begins with homogeneous nanoscale surface texture, and as the material is stretched linearly by 200%, or multilaterally by 225%, the surface breaks apart into microscale agglomerates which maintain nanoscale texture at their surface. The surface of a natural lotus leaf has microscale protrusions that are covered in very fine nanoscale hairs. The hierarchical texture contributes to the plant's strong hydrophobicity and strongly resembles the surface structure of stretched latex coatings disclosed herein.

The Cassie-Baxter model of wetting dictates that textured contact angle ($\theta_{CB}$) increases over the contact angle of the flat material ($\theta$) as the area fraction of contact between the liquid and the surface ($\varphi$) decreases:

$$\cos \theta_{CB} = \varphi(1+\cos \theta)-1 \qquad \text{Equation (1)}$$

This suggests that the formation of microscale agglomerates caused by stretching could lower the contact area and lead to an increase hydrophobicity.

FIG. 17 shows the contact angle of an embodiment of the superhydrophobic latex coating as it is stretched linearly to 1.75 times the original length. There is a steady increase in contact angle with increasing stretch length. The increase continues for stretching up to triple the original length, as shown in FIG. 10. The increase in Cassie-Baxter state contact angle ($\theta_{CB\text{-}stretch}$) can be modeled by modifying the classic Cassie-Baxter equation to account for decrease in contact fraction with increased stretch (S):

$$\cos \theta_{CB\text{-}stretch} = \varphi/S(1+\cos \theta_{CB})-1 \qquad \text{Equation (2)}$$

In this model, a simple assumption has been made that gaps opened by stretching are not available for liquid contact. Equation 2 applies only in the case of linear stretching; unilateral stretching would not result in linear decrease in contact fraction. Equation 2 is plotted in FIG. 17 and it matches the upward trend observed in the experimental data. Stretching certain embodiments of the stretchable superhydrophobic coating disclosed herein increases its hydrophobicity. First, with moderate stretching there is a sharp increase in contact angle that can be attributed to the tendency of the liquid to maintain surface contact even as stretching introduces microtexture. A hybrid Wenzel/Cassie-Baxter model is fit to experimental data. After the hybrid regime, the contact angle declines and then steadily climbs with further stretching. This trend is attributed to the transition from homogeneous nanotexture to hierarchical micro- and nanotexture caused by stretching. The curve fit to the experimental data is an extension of the classic Cassie-Baxter model that accounts for the decrease in surface contact fraction that is caused by stretching. Error bars show standard deviation (N=5).

There is also a sharp increase in contact angle with moderate stretching (up to ~11%) seen in FIG. 17 that Equation 2 cannot account for. It is thought that during light stretching, there is a new hybrid wetting state that combines the Cassie-Baxter and Wenzel models. In the Wenzel regime, the full surface area of the material remains in contact with the impinging liquid. Recall that in the classic Wenzel model for wetting, the contact angle ($\theta_w$) of a textured surface increases as the ratio of the actual surface area over its projected surface area ($r_o$) increases:

$$\cos \theta_w = r_o \cos \theta \qquad \text{Equation (3)}$$

In the proposed model for the hybrid Wenzel/Cassie-Baxter state, at start is an assumption that the liquid is in a Cassie-Baxter wetting state with contact points in a plane parallel to the surface of the unstretched homogeneously nanotextured layer. Under moderate stretching, it is assumed that the contact fraction remains constant even as moderate microtexture is introduced. That is, it is proposed that liquid maintains its partial contact even as contact points become non-planar. A diagram to illustrate the proposed hybrid wetting state is shown in FIG. 25.

Figure 25:
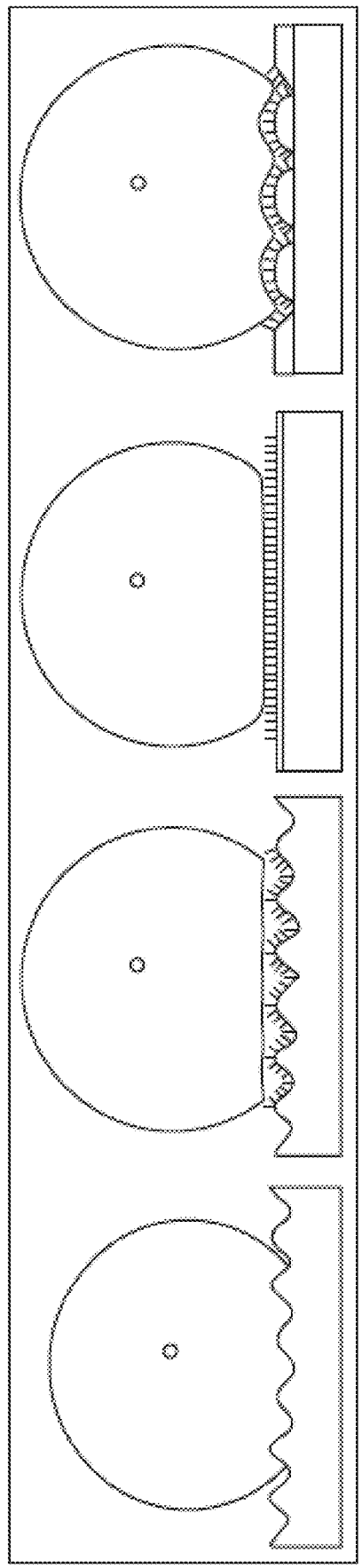
FIG. 25 shows an additional schematic illustration comparing the micro- and nanostructure of water droplets on unitary and combination hydrophobic surfaces. Wenzel state wetting over microtexture is shown in the far left illustration. Cassie-Baxter state wetting over hierarchically structures micro- and nanotexture is shown in the middle left illustration. Cassie-Baxter state wetting over nanotexture is shown in the middle right illustration, and the hybrid Wenzel/

FIG. 25 is a diagram of the wetting states induced by surface texture. From left to right is: Wenzel state wetting over microtexture, Cassie-Baxter state wetting over hierarchical micro- and nanotexture structures, Cassie-Baxter state wetting over nanotexture, and the hybrid Wenzel/Cassie-Baxter state wetting over a stretching nanotextured surface. In classic wetting theory, there are two regimes where texture causes an increase in contact angle. In the Wenzel regime (the first state shown in FIG. 25), the liquid maintains continuous surface contact. In the hierarchical Cassie-Baxter regime (the second state), the liquid contact is discontinuous and heterogeneous, only occurring at the uppermost region of microscale features. Homogeneous nanotexture (the third state) can also result in Cassie-Baxter regime wetting where contact points are homogeneously distributed. When homogeneous nanotexture is embedded in a flexible material and stretched it begins to form microscale gaps, which results in a hybrid wetting state (the fourth state shown in FIG. 25), where contact is homogenous despite the presence of microscale features.

As this is similar to what happens in the classic Wenzel regime, Equation 3 is used as the basis for the hybrid model. It is assumed that stretching leads to a proportional increase in projected surface area. The contact angle in this state ($\theta_{w\text{-}stretch}$) is given by Equation 4:

$$\cos \theta_{w\text{-}stretch} = Sr_o \cos \theta \qquad \text{Equation (4)}$$

It can be seen in FIG. 17 that this regime results in a sharp increase in contact angle even with moderate stretching. In fact, the increase is tempered somewhat by the fact that the Cassie-Baxter stretching state (Eqn. 2) still applies. The line plotted in FIG. 17 is an equally weighted average of the contact angles given by Eqns. 2 and 4: $\theta_{hybrid}=(\theta_{CB\text{-}stretch}+\theta_{w\text{-}stretch})/2$. Nonetheless, the contact angle quickly reaches its limit (180°), and beyond a moderate level of stretching, the hybrid regime no longer applies. In the experimental data, this is borne out by a decline after 8% stretching followed by a more moderate contact angle increase with continued stretching.

Equations for hybrid wetting state and the stretching Cassie-Baxter state are fit to experimental data in FIG. 17 by assuming that the water contact angle of HMDS is 100 degrees and using this value, the experimentally measured Cassie-Baxter state contact angle (155.4°), and Equation 1 to calculate p. The projected surface area ratio, $r_o$, from the Wenzel regime is calculated similarly. The theoretical limit of stretching for the hybrid wetting state under these experimental parameters is 1.11 (the dashed line in FIG. 17), although it can be seen that the contact angle begins to decline prior to reaching this limit. It is well known that the Cassie-Baxter wetting state becomes energetically unfavorable as the contact angle approaches 180° and it is assumed that this applies to the hybrid state as well.

Interestingly, the hybrid wetting state is also observed during relaxation from a stretched state. The same characteristic increase in contact angle for moderate stretching is seen in a sample that has already been stretched to three times the original length. Upon complete relaxation, the contact angle is elevated relative to the unstretched condition. This suggests that the formation of microtexture by stretching is partially but not completely reversible. In any case, stretching and relaxing certain embodiments of the material leads to improved hydrophobicity.

The response of certain embodiments of the latex-based superhydrophobic material to stretching is counter-intuitive because external stress usually leads to a decline in hydrophobicity in textured materials. The ability of this phenomenon extending to other types of stress was tested using a simple method to measure durability against abrasion. FIGS. 15 and 16 show the change in contact angle and roll-off angle after multiple abrasion cycles. Aggressive abrasion typically results in a significant decline in hydrophobicity for textured materials. In each case here, the experiment was stopped when the underlying latex failed, usually by tearing.

When the latex was fully dried (at least 1 week), the material sustained high hydrophobicity until the underlying latex succumbed to the aggressive scraping and tore, which came after 5 or 6 abrasion cycles. Further drying time for the coating (1 month) ensured a low roll-off angle through multiple abrasions. Overall, the material exhibited significant durability, which can be attributed to the ability of silica fibers to yield and bend within the latex rather than shear off. The latex-based superhydrophobic material is also robust to multiple stretch and relaxation cycles, as only a modest decline in hydrophobicity was seen after 100 stretch cycles to 1.75 original length.

Close examination of the wetting behavior in the hydrophobic materials disclosed herein revealed an unexpected increase in hydrophobicity with stretching. Transition from heterogeneous nanotexture to hierarchical micro/nanotexture may be responsible for the steady increase in contact angle with stretching. An interesting aspect of the wetting behavior of the stretchable superhydrophobic material is the sharp increase in contact angle with only moderate stretching. A hybrid wetting theory for moderate stretching and an extension of the Cassie-Baxter theory for extended stretching is presented, that borrows from the principles of the classic Wenzel and Cassie-Baxter theories. The condition that precipitates transition between the two regimes is not yet clear, except to say that very high contact angles become energetically unfavorable under any conditions. For this reason, the hybrid wetting state may only exist with moderate stretching. While the hybrid theory is presented in the context of stretching superhydrophobic materials, it may be broadly useful for the design of new inelastic superhydrophobic materials.

Stretchable materials that take advantage of the hybrid wetting state may broaden the potential applications for superhydrophobic coatings. For example, personal protective equipment (e.g., gloves, clothing, shoes, etc.) with modified wetting behavior such that liquids are shed easily may reduce the risks of transmitting infectious disease. This may be especially effective at reducing the risk to healthcare workers who treat patients with blood borne and contact transmitted diseases such as AIDS and Ebola. The materials disclosed herein are non-toxic and the processes inexpensive, so the coating could be integrated into disposable items. Stretching will allow hydrophobicity to endure and even improve for short durations of use.

Herein are described processes, comprising applying a stretchable, hydrophobic coating to a substrate by dispensing liquid polymer to the substrate forming a layer of liquid polymer thereon, and embedding a plurality of hydrophobic particles in the layer of liquid polymer, to form a coating on the substrate that is hydrophobic and stretchable. Embodiments of any of the disclosed processes may further comprise the step of drying the liquid polymer.

In embodiments of any of the processes described herein, the liquid polymer may comprise latex, nitrile, polydimethylsiloxane or a mixture thereof. In additional embodiments of any of the processes described herein, the substrate may comprise latex and/or nitrile. In further embodiments of any of the processes described herein, the hydrophobic particles may comprise silica or polytetrafluoroethylene. In yet additional embodiments of any of the processes described herein, the hydrophobic particles may comprise a hydrophobic shell.

Embodiments of the stretchable, hydrophobic coatings made with any of the disclosed processes may exhibit a measurable increase in water contact angle when stretched unilaterally to a length between about 110% to about 300% of its original length. The stretchable, hydrophobic coatings made with any of the disclosed processes may, in some embodiments, retain their hydrophobicity after at least four abrasion cycles. The stretchable, hydrophobic coatings made with any of the disclosed processes may, in further embodiments, exhibit high fluid droplet mobility with a roll-off angle not greater than 20 degrees. Additional embodiments of the stretchable, hydrophobic coatings made with any of the disclosed processes may both retain their hydrophobicity after at least four abrasion cycles and exhibit high fluid droplet mobility with a roll-off angle not greater than 20 degrees.

In some embodiments, articles, including a glove or a bandage, may comprise the stretchable, hydrophobic coatings made with any of the disclosed processes.

Also described herein are processes, comprising rendering a stretchable surface hydrophobic by dispensing liquid polymer to a stretchable surface forming a layer of liquid polymer thereon, and embedding a plurality of hydrophobic particles into the layer of liquid polymer to form a hydrophobic surface, wherein the hydrophobic surface exhibits an increase in water contact angle when stretched unilaterally to a length between about 110% to about 300% of its original length.

In embodiments of any of the processes described herein, the liquid polymer may comprise latex, nitrile, or polydimethylsiloxane. In additional embodiments of any of the processes described herein, the substrate may comprises latex and/or nitrile. In further embodiments of any of the processes described herein, the hydrophobic particles comprise silica or polytetrafluoroethylene.

Further described herein are processes, comprising manufacturing a stretchable, hydrophobic glove by dispensing liquid polymer to the outer surface of a stretchable glove forming a layer of liquid polymer thereon, applying a plurality of hydrophobic particles to the liquid layer of polymer such that at least a portion of the plurality of particles are embedded into the liquid layer of polymer, and drying the liquid layer of polymer.

In embodiments of any of the processes described herein, the liquid polymer may comprise latex, nitrile, or polydimethylsiloxane. In additional embodiments of any of the processes described herein, the substrate may comprise latex and/or nitrile. In further embodiments of any of the processes described herein, the hydrophobic particles may comprise polytetrafluoroethylene and/or silica coated with hexamethyldisilazane, polydimethylsiloxane or a mixture thereof.

Additionally described herein are coating compositions, comprising a plurality of hydrophobic particles and a polymer, wherein at least a portion of the plurality of the hydrophobic particles are embedded in the polymer, and wherein the composition forms a stretchable and hydrophobic coating.

In embodiments of any of the coating compositions described herein, the hydrophobic coating may exhibit an increase in water contact angle when stretched. In further embodiments of any of the coating compositions described herein, the hydrophobic coating may retain its hydrophobicity after at least four abrasion cycles. In further embodiments of any of the coating compositions described herein, the hydrophobic coating may exhibit high fluid droplet mobility with a roll-off angle not greater than 20 degrees.

In embodiments of any of the coating compositions described herein, the plurality of hydrophobic particles may comprise a plurality of silica particles having a hexamethyldisilazane shell. In further embodiments of any of the coating compositions described herein, the plurality of hydrophobic particles may comprise a plurality of silica particles having a polydimethylsiloxane shell. In additional embodiments of any of the coating compositions described herein, the plurality of hydrophobic particles may comprise a plurality of silica particles having a mixture of hexamethyldisilazane and polydimethylsiloxane shells.

In embodiments of any of the coating compositions described herein, the polymer may be latex or nitrile. In additional embodiments of any of the coating compositions described herein, the composition may form a superhydrophobic and stretchable coating when applied to a substrate.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A process, comprising:
   applying a stretchable, hydrophobic coating to a substrate by dispensing liquid polymer to the substrate forming a layer of liquid polymer thereon,
   partially embedding a plurality of hydrophobic particles in the layer of liquid polymer, to form a coating on the substrate that is hydrophobic and stretchable, wherein the plurality of hydrophobic particles contains aggregate fibers.

2. The process of claim 1, wherein the liquid polymer comprises latex, nitrile, polydimethylsiloxane or a mixture thereof.

3. The process of claim 1, wherein the substrate comprises latex and/or nitrile.

4. The process of claim 1, wherein the hydrophobic particles comprise silica or polytetrafluoroethylene.

5. The process of claim 1, wherein the hydrophobic particles comprise a hydrophobic shell.

6. The process of claim 1, further comprising the step of drying the liquid polymer.

7. The process of claim 1, wherein the stretchable, hydrophobic coating exhibits a measurable increase in water contact angle when stretched unilaterally to a length between about 110% to about 300% of its original length.

8. The process of claim 1, wherein the hydrophobic coating retains its hydrophobicity after at least four abrasion cycles;
   wherein the hydrophobic coating exhibits high fluid droplet mobility with a roll-off angle not greater than 20 degrees; or both.

9. The process of claim 1, wherein the aggregate fibers are between about 100 nm and about 300 nm in length.

10. The process of claim 1, wherein the plurality of hydrophobic particles further comprises agglomerates between about 100 nm and about 1000 nm in length.

11. An article comprising a stretchable, hydrophobic coating prepared by claim 1.

12. The article of claim 11, wherein the article is a glove or a bandage.

13. A process, comprising:
    rendering a stretchable surface hydrophobic by dispensing liquid polymer substantially free of hydrophobic particles to a stretchable surface forming a layer of liquid polymer thereon, and
    embedding a plurality of hydrophobic particles into the layer of liquid polymer to form a hydrophobic surface, wherein the plurality of hydrophobic particles comprises aggregate fibers,
    wherein the hydrophobic surface exhibits an increase in water contact angle when stretched unilaterally to a length between about 110% to about 300% of its original length.

14. The process of claim 13, wherein the liquid polymer comprises latex, nitrile, or polydimethylsiloxane; and the substrate comprises latex and/or nitrile.

15. The process of claim 13, wherein the hydrophobic particles comprise silica or polytetrafluoroethylene.

16. A process, comprising:
    manufacturing a stretchable, hydrophobic glove by dispensing liquid polymer substantially free of hydrophobic particles to the outer surface of a stretchable glove forming a layer of liquid polymer thereon,
    applying a plurality of hydrophobic particles to the liquid layer of polymer such that at least a portion of the plurality of particles are partially embedded into the liquid layer of polymer, wherein the plurality of hydrophobic particles comprises aggregate fibers, and wherein the plurality of hydrophobic particles comprising aggregate fibers that form hierarchical microstructured and nanostructured features when stretched linearly by about 200% or more; and drying the liquid layer of polymer.

17. The process of claim 16, wherein the liquid polymer comprises latex, nitrile, or polydimethylsiloxane; the substrate comprises latex and/or nitrile; and the hydrophobic particles comprise polytetrafluoroethylene and/or silica coated with hexamethyldisilazane, polydimethylsiloxane or a mixture thereof.

18. A coating composition, comprising a plurality of hydrophobic particles and a polymer, wherein at least a portion of the plurality of the hydrophobic particles are partially embedded in the polymer, wherein the composition forms a stretchable and hydrophobic coating, and wherein the plurality of hydrophobic particles comprises aggregate fibers and agglomerates.

19. The composition of claim 18, wherein the hydrophobic coating exhibits an increase in water contact angle when stretched; and/or retains its hydrophobicity after at least four abrasion cycles; and/or exhibits high fluid droplet mobility with a roll-off angle not greater than 20 degrees.

20. The composition of claim 18, wherein the plurality of hydrophobic particles comprises a plurality of silica particles having a hexamethyldisilazane shell, a polydimethylsiloxane shell, or a mixture thereof, wherein the polymer is latex or nitrile, and wherein the composition forms a superhydrophobic and stretchable coating when applied to a substrate.

* * * * *